(12) United States Patent
Hughes

(10) Patent No.: US 9,334,098 B1
(45) Date of Patent: May 10, 2016

(54) REACTIVE MATERIALS PACKAGING

(76) Inventor: Kenneth D. Hughes, Alpharetta, GA (US)

( * ) Notice: Subject to any disclaimer, the term of this patent is extended or adjusted under 35 U.S.C. 154(b) by 1580 days.

(21) Appl. No.: 11/089,703

(22) Filed: Mar. 25, 2005

Related U.S. Application Data

(60) Provisional application No. 60/557,147, filed on Mar. 26, 2004.

(51) Int. Cl.
*B65D 81/32* (2006.01)

(52) U.S. Cl.
CPC .................................. *B65D 81/3266* (2013.01)

(58) Field of Classification Search
CPC .................................................. B65D 81/3266
USPC ............ 206/219–222, 568; 222/94, 105–107, 222/130, 145.5–145.6; 422/58, 61, 422/100–102; 436/177–180
See application file for complete search history.

(56) References Cited

U.S. PATENT DOCUMENTS

| | | | |
|---|---|---|---|
| 3,344,061 A | 9/1967 | Kellum | |
| 3,799,742 A * | 3/1974 | Coleman | 422/61 |
| 4,084,747 A | 4/1978 | Alliger | |
| 4,093,188 A | 6/1978 | Horner | |
| 4,251,224 A | 2/1981 | Cowley et al. | |
| 4,330,531 A | 5/1982 | Alliger | |
| 4,462,224 A * | 7/1984 | Dunshee et al. | 206/219 |
| 4,528,180 A | 7/1985 | Schaeffer | |
| 4,585,482 A | 4/1986 | Tice et al. | |
| 4,632,568 A | 12/1986 | Emele et al. | |
| 4,683,039 A | 7/1987 | Twardowski et al. | |
| 4,952,068 A | 8/1990 | Flint | |
| 4,997,083 A * | 3/1991 | Loretti et al. | 206/219 |
| 4,998,671 A * | 3/1991 | Leifheit | 206/219 |
| 5,126,070 A | 6/1992 | Leifheit et al. | |
| 5,290,518 A * | 3/1994 | Johnson | 422/58 |
| 5,360,609 A | 11/1994 | Wellinghoff | |
| 5,593,804 A * | 1/1997 | Chemelli et al. | 430/30 |
| 5,650,446 A | 7/1997 | Wellinghoff et al. | |
| 5,674,653 A * | 10/1997 | Chemelli et al. | 422/61 |
| 5,804,546 A | 9/1998 | Hall | |
| 5,866,003 A | 2/1999 | Okubo et al. | |
| 6,051,135 A | 4/2000 | Lee et al. | |
| 6,135,632 A | 10/2000 | Flint | |

(Continued)

FOREIGN PATENT DOCUMENTS

| | | | |
|---|---|---|---|
| JP | 2000211901 | | 8/2000 |
| WO | WO 95/05327 | * | 2/1995 |
| WO | WO 2004/071960 A2 | | 8/2004 |

OTHER PUBLICATIONS

U.S. Appl. No. 11/432,259, filed May 11, 2006.

(Continued)

*Primary Examiner* — Bryon Gehman
(74) *Attorney, Agent, or Firm* — F. Brent Nix, Esq.; Johnson, Marcou & Isaacs, LLC

(57) ABSTRACT

Devices are disclosed for the generation and containment of reactive treatment agents. Formulations containing these agents can be applied widely as disinfectants, odor control agents, decontamination and fumigation agents, liquid, gas, and air treatment materials, respiratory agents, food and beverage processing agents, neutralization agents, nutritional and dietary supplements, and in many industrial, residential, medical and military surface treatment operations.

17 Claims, 5 Drawing Sheets

(56) References Cited

U.S. PATENT DOCUMENTS

| | | | |
|---|---|---|---|
| 6,203,688 B1 | 3/2001 | Lipsztajn et al. | |
| 6,238,643 B1 | 5/2001 | Thangaraj et al. | |
| 6,319,243 B1 * | 11/2001 | Becker et al. | 206/568 |
| 6,355,093 B1 | 3/2002 | Schwartz et al. | |
| 6,428,696 B2 | 8/2002 | Kuke | |
| 6,432,322 B1 | 8/2002 | Speronello et al. | |
| 6,451,253 B1 | 9/2002 | Pitochelli et al. | |
| 6,458,735 B1 | 10/2002 | Klatte | |
| 6,503,419 B2 | 1/2003 | Klatte | |
| 6,583,103 B1 | 6/2003 | Klinkhammer | |
| 6,602,466 B2 * | 8/2003 | Hamilton et al. | 422/37 |
| 6,605,304 B1 | 8/2003 | Wellinghoff et al. | |
| 6,607,696 B1 * | 8/2003 | Hamilton et al. | 206/219 |
| 6,638,900 B2 | 10/2003 | Ajmani | |
| 6,689,736 B2 | 2/2004 | Thomas et al. | |
| 6,764,661 B1 | 7/2004 | Girard | |
| 6,790,427 B2 | 9/2004 | Charles et al. | |
| 7,201,841 B2 | 4/2007 | Hughes | |
| 7,243,788 B2 * | 7/2007 | Schmidt et al. | 206/221 |
| 7,383,946 B2 | 6/2008 | Hughes | |
| 2004/0149634 A1 | 8/2004 | Hughes | |
| 2006/0289349 A1 | 12/2006 | Hughes | |

OTHER PUBLICATIONS

U.S. Appl. No. 11/089,682, filed Mar. 25, 2005.

* cited by examiner

Figure 1A and 1B:
1A
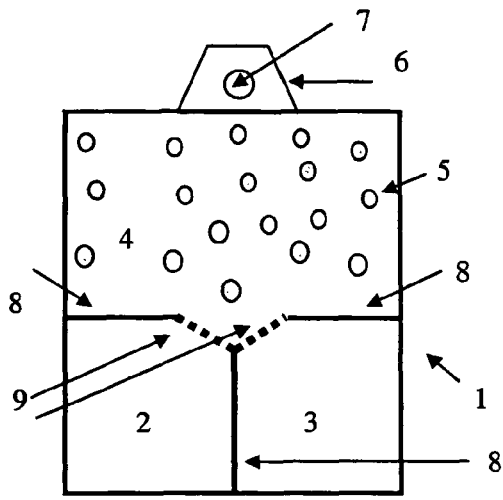
1B
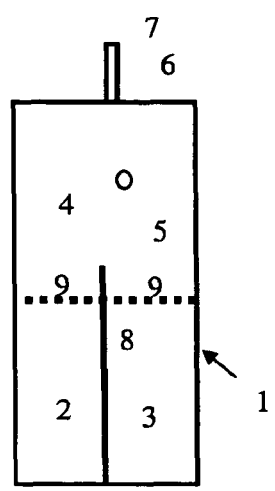
Figure 2A, 2B, 2C
2A
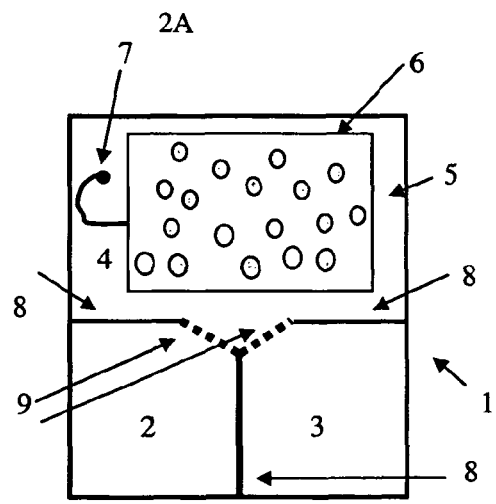
2B
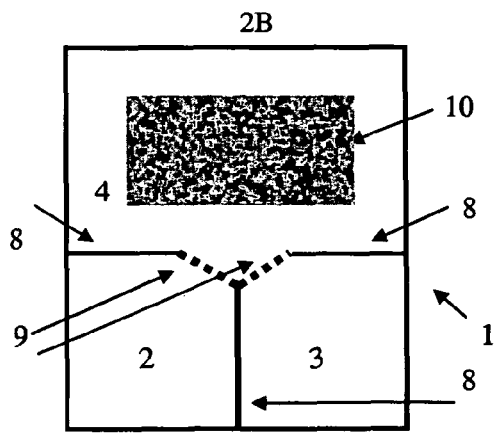
Figure 2C
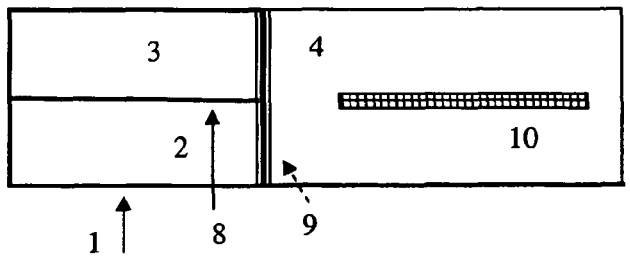

3A

3B

Figure 9:
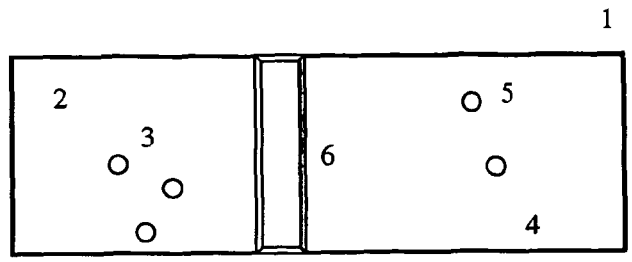
Figure 10A and 10B:
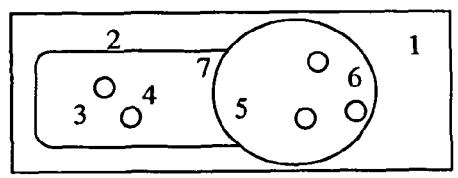 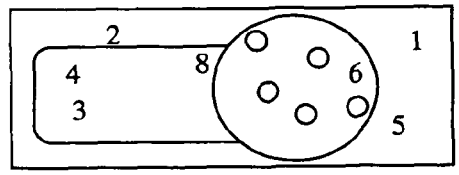
Figure 11.
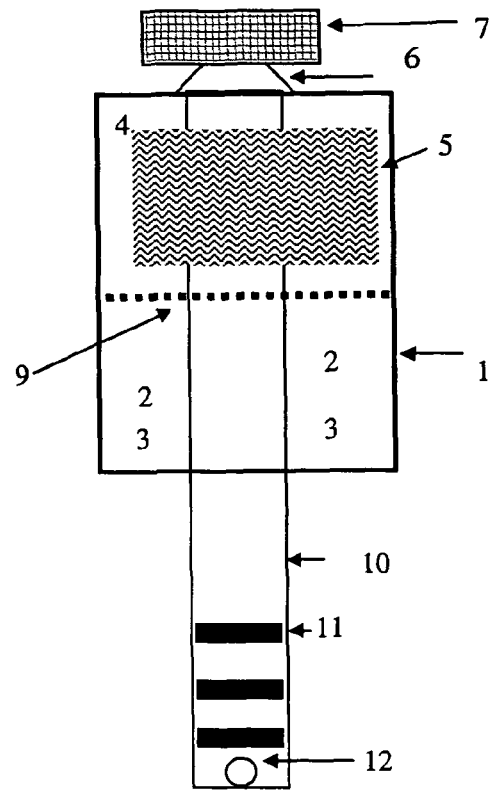

REACTIVE MATERIALS PACKAGING

CROSS-REFERENCE TO RELATED APPLICATION

This application claims priority to and the benefit of the filing date of U.S. provisional application, Ser. No. 60/557,147, entitled "Reactive Materials Packaging," filed on Mar. 26, 2004, which is entirely incorporated herein by reference.

FIELD OF THE INVENTION

The herein disclosed invention is directed at devices fabricated with flexible polymer films, rigid polymer components, and combinations thereof, combined with methods for the generation, containment, and manipulation of useful chemical and biological agents including gases, colloids, precipitates, and complex mixtures thereof, inside these devices, and for delivery of these useful agents outside the device for surface and fluid treatment applications. Devices of the invention provide safe, convenient, and inexpensive preparation of highly reactive treatment materials which can be applied as disinfectants, odor control agents, decontamination and fumigation agents, gas and air treatment materials, respiratory agents, food and beverage processing and preparation agents, nutritional and dietary supplements, chemical and biological neutralization agents, and for preparing solutions and substrates for porous and nonporous surface cleaning operations in many industrial, residential, medical, and military situations.

BACKGROUND OF THE INVENTION

Highly reactive solids, liquids, and gases are used for a wide range of operations involving the treatment, cleaning, sanitizing, and decontaminating of porous and nonporous surfaces, liquids, and local gaseous environments. Often, a very concentrated form of the reactive treatment agent is used to prepare lower concentration solutions for use in the operation. Additionally, materials in related forms are used to improve food and beverage quality, and even to prepare nutritional supplements. Further, applicators or substrates are often used to introduce the highly reactive treatment agents to the gas, liquid, or solid, that is undergoing treatment.

While there are many highly reactive gas, liquid, and solid treatment agents which are used in independent fashion, it is customary to prepare multi-component compositions for direct introduction into a fluid or onto a surface. One of the most often used class of reactive treatment agents is oxidizing agents. These agents are available in solid, liquid, and gas forms. Exemplary oxidizing agents include peroxides, peracids, percarbonates, persulfates, dissolved halogenated compounds, and reactive gases such as chlorine, chlorine dioxide, ozone, sulfur dioxide, and oxygen. Another class of highly useful treatment agents includes natural and synthetic minerals, adsorbents, and resins with varying surface properties. Often times these agents can be colloids, precipitates, and particulates of nanometer dimensions. Agents in these classes are often mixed with adjunct agents to form complex solutions. Adjunct agents can be used to modify solution parameters and to provide indication of solution properties. Exemplary adjunct agents include minerals, surfactants, foam control agents, wetting agents, solubility agents, flocculating agents, biocides, and gases. Often, synergy between formulation components can be obtained.

In many operations the use of applicators, substrates, of combinations thereof facilitates the use of reactive treatment agents. Suitable substrates include adsorption and absorption materials, woven and nonwoven materials, porous materials and supports, and solid elements which allow manipulation of substrates which contains the active treatment agents.

It is well understood that many different types of surface bound and dissolved contaminants exist in a variety of situations found in residential, industrial, medical, and military fields, and that many different reactive agents and treatment formulations are required to successfully address all contaminant types. It is also well understood that treatment operations of all types are more successful when freshly prepared reactive treatment agents are used. As a result, small volume batches of reactive agents are prepared in order to treat both chemical and biological contaminants. Batches of reactive treatment agents are prepared frequently through dissolution, dilution, activation, or a combination thereof of a highly concentrated form of the reactive treatment agent, and formulations which contain these agents.

While repetitive preparation of fresh highly reactive treatment agents is optimal for the treatment operation it also increases the hazards to personnel and equipment. Training and experience are thus required for use of many highly reactive agents. Unfortunately, these issues frequently limit the widespread use of many highly efficacious reactive treatment agents.

The instant invention discloses devices in the form of thin film packages and molded plastic components which facilitate the simple, safe, economical, and reagent efficient generation and containment of reactive treatment agents. The disclosed devices further provide a safe and controlled method for applying the instantly prepared treatment agents to surfaces and fluids for the reduction of contaminants and the introduction of beneficial agents to fluid systems.

Exemplary reactive treatment agents of the invention include complex mixtures containing, oxidizing agents, reducing agents, colloids, surfactants, acids, bases, metal precipitates, and adjuncts such as foam control agents, viscosity modifiers, surfactants, thickeners, and solution stabilizers.

Devices of the invention can not be used as filters, as they function by delivering reactive treatment agents onto surfaces or into fluids without the bulk transfer of the contaminated fluid undergoing treatment into or through the device. Since the ability to pass bulk gas, water or other aqueous liquids containing contaminants through the device is not present, devices do not reduce fluid contaminants by filtration mechanisms. This predefined system feature is highly advantages and allows these devices to be applied in a very wide range of environments, including extreme environments such as underwater and in small spaces.

DESCRIPTION OF RELATED ART

Batches of highly reactive treatment agents can lose their effectiveness over time and are best used immediately after preparation. Effectiveness of reactive agents is decreased due to a range of factors including loss to the surroundings, reaction with containers and housings, and breakdown or reaction with light, air, elevated temperature, and other formulation components. As a result, new batches of reactive treatment agents must be continually prepared. In order to increase operator safety, reduce material waste, and improve the economics of treatment operations, batches of highly reactive treatment agents should be prepared in accordance with the specific size and needs of the operation.

Common examples of current batch preparation practice include use of halogens and more specifically hypochlorite based cleaning and sanitizing products. The use of chlorine gas and powdered chlorine allow liquid solutions of highly reactive hypochlorous acid to be generated. These solutions lose effectiveness over time as this highly reactive treatment agent can easily be lost as a result of reaction with solution components and light.

Another common example includes adhesive preparation, which often involves the combination of two components which are very reactive with each other. By tuning the formulation, the adhesive can be manipulated for several minutes and applied before it becomes unusable. In addressing this very unique application, one-time use sachets, syringes, and mixing tubes specialized for preparing adhesives have been developed. These devices in simplest form consist of two or more separate containers each housing one component of the formula. In practice, adhesive components simultaneously exit the individual containers and are mixed manually before application. Devices for adhesive preparation with greater complexity involve a single housing which is segmented into multiple component chambers. Exemplary art is disclosed in U.S. Pat. No. 4,093,188, U.S. Pat. No. 4,632,568, U.S. Pat. No. 6,135,632, and U.S. Pat. No. 4,952,068.

Multi-component cleaning solutions that mix liquid streams upon exiting a multi-chambered container have been developed. Products based upon this concept have targeted personal care and residential cleaning applications. Common systems of this type are disclosed in U.S. Pat. No. 4,330,531, U.S. Pat. No. 4,528,180, U.S. Pat. Nos. 5,804,546, 6,638,900, and U.S. Pat. No. 6,583,103. Similarly, convenience is being addressed through development of previously prepared cleaning wipes. Exemplary art includes U.S. Pat. No. 6,689,736.

There is a continuing need for the preparation of highly reactive treatment agents and methods for their use in all fields. Paralleling this need is the desire to improve both the safety and economics of reactive treatment agent generation, delivery, and application.

SUMMARY OF THE INVENTION

The instant invention involves devices in the form of thin film packages and molded component housings which facilitate the generation, manipulation, and storage of reactive treatment agents inside the sealed devices. Further, the devices of the invention allow controlled delivery of the generated reactive treatment agents from the device and onto surfaces for surface treatment and into fluids for contaminant reduction and beneficial agent introduction.

Reactive treatment agents and the precursors which yield these agents are manipulated and controlled by several integrated device mechanisms including pressure and chemical sensitive barriers, integrated mixing elements, predefined permeable films, chemical constituents which change the physical and chemical properties of contained solutions, and particulate or fiber matter that absorbs fluids and constituents carried by this fluids in dissolved or suspended states. Preferred reactive agents are gases and preferred fluid control mechanisms allow fluids to be absorbed with dissolved gases.

Devices of the invention, which generate reactive treatment agents, of the invention, are suitable for the direct treatment of local atmospheres, liquids, and surfaces and for the preparation of secondary solutions and materials which will be used in treating local atmospheres, liquids, and surfaces.

Devices of the invention include packages prepared in a manner which partition reactive agent precursors and reactive treatment agents in discrete compartments or chambers specialized for different functions. Compartments are designed for storage of reactive agent precursors, mixing of precursors, storage of the generated reactive treatment agents, combination of agents with optional adjuncts, and delivery of the reactive treatment agents and optional adjuncts to a surrounding atmosphere, liquid, solution, or surface. Devices may incorporate liquids, solids, gases, or a combination thereof.

Single use devices and methods of the invention are ideally suited for preparing batches of highly reactive treatment agents and rapidly formulating these agents with adjuncts for specific applications. Immediate preparation before use of the reactive treatment agent maximizes agent efficacy. Since reactive agent preparation is completed in an enclosed system and only in the amounts required, both safety and economy is maximized. Exemplary materials, methods, and devices include use of oxidizing agents, reducing agents, acids, bases, anions, cations, freshly prepared colloids and precipitates, and reactive gases including but not limited to, chlorine dioxide, carbon dioxide, oxygen, sulfur dioxide, chlorine containing gases, and nitrogen containing gases.

The utility of the instant invention is far reaching and provides significant benefits that have not been previously described in the field of devices designed and fabricated for the optimum generation, manipulation, storage, delivery, and application of highly reactive treatment agents.

It is therefore an object of this invention to provide devices and methods for preparing reactive agents for treating porous and nonporous surfaces, and porous and nonporous materials. It is a further object of this invention to provide devices for preparing decontamination materials useful for industrial, medical and military applications. Furthermore, it is an object of this invention to provide devices which can generate unique laundry and textile treatment formulations which include commonly used washing and drying adjuncts.

It is an object of this invention to provide devices which generate materials for treating gaseous systems such as the local atmosphere, enclosed structures, ventilation systems, and breathing air for chemical and biological contaminants, without the need for passing the fluid through filters or using filtration technology.

It is a further object of the invention to provide devices which generate materials for treating local and enclosed atmospheres for odors, without the need for passing the fluid through filters or using filtration technology.

Furthermore it is an object of this invention to provide devices which can generate materials for odor treatment in the food, animal care, waste treatment, petroleum, chemical, medical, and health industries, without the need for passing fluid through filters or using filtration technology.

It is an object of this invention to provide devices which can generate materials that can be used for sanitization, disinfection, the sterilization and maintenance of sterile conditions, for objects and materials associated with hospital, medical, surgical, and dental use. It is a further object of this invention to provide devices which can generate materials that can simultaneously absorb medical wastes and release a medical waste treatment agent. Furthermore it is an object of this invention to provide devices which can generate materials which can be used in the treating of wounds, sores, and skin conditions. It is an object of this invention to provide devices which can generate materials for personal hygiene and infant care.

It is an object of this invention to provide devices that can generate materials to treat fluids such as fuels, lubricants, and cutting fluids, which contain water, biological, and chemical contaminants, without the need for passing fluid through filters or using filtration technology.

Further it is an object of this invention to provide devices which generate materials that treat fuels by simultaneously removing water and releasing biological control agents, without the need for passing fluid through filters or using filtration technology.

It is another object of this invention to provide devices for generating materials that can simultaneous secure a chemical or biological military agent in liquid or powder form, neutralize, and breakdown these agents.

It is an object of this invention to provide devices, materials, and methods for controlling and treating foods and associated liquids present during preparation, delivery, and storage of food.

It is an object of this invention to provide devices which generate materials for treating recreational water systems, such as pools and spas for chemical and biological contaminants, without the need for passing fluid through filters or using filtration technology.

Further it is an object of the invention to provide devices which generate treatment materials for recreational water systems that include commonly used adjuncts.

It is an object of this invention to produce devices that incorporate visual indicators for determining the remaining lifetime of the device, remaining lifetime of materials contained by the device, or combinations thereof.

Further, it is an object of this invention to provide devices and materials that can relate gas concentration to surrounding temperature and pressure characteristics associated with packaged articles.

It is also an object of this invention to provide devices and materials for inclusion, adherence, or combination thereof, to packaged articles. Further, it is an object of the invention to provide devices and materials which can be adhered to products stored in enclosed systems, such as refrigerators, coolers, and freezers.

It is also an object of this invention to provide devices which can activate and deliver viable organisms, cells, and their components as well as proteins, enzymes, and genetic material.

It is an object of the invention to provide devices for generating materials that treat aqueous solutions such as potable water for biological and chemical contamination, without the need for passing fluid through filters or using filtration technology.

Further it is an object of this invention to provide devices that generate materials that treat potable water for taste and odor, without the need for passing fluid through filters or using filtration technology.

Furthermore, it is an object of the invention to provide devices which can simultaneously deliver a highly reactive treatment agent and a nutritionally beneficial agent to potable water.

It is also an object of the invention to prepare devices for generating materials that treat beverages for chemical and biological contamination, as well as for taste and odor, without the need for passing fluid through filters or using filtration technology.

It is an object of this invention to prepare devices which generate materials for treating waste water, industrial effluent, cooling and boiler water, for chemical and biological contaminants and in combination with commonly used adjuncts, without the need for passing fluid through filters or using filtration technology.

It is an object of this invention to prepare devices which generate organic colloids, inorganic, colloids, and combinations thereof, for health and wellness products. It is a further object of this invention to provide devices which generate formulations containing these materials and additional compounds such as nutritionals, nutraceuticals, pharmaceuticals, or combinations thereof. It is a still further object of this invention to prepare devices which generate these materials in a manner that provides an indication of activation including visual changes and temperature changes.

BRIEF SUMMARY OF FIGURES

FIG. 1A, a top view, illustrates one embodiment of the invention, a sealed package made from polymer films, containing two reactive precursor compartments, and one mixing and storage compartment. The compartments are prepared using two polymer sheets. FIG. 1B, a side view, illustrating a similar embodiment of the invention, a sealed package made from polymer films, containing two reactive precursor compartments, and one mixing and storage compartment. The compartments are prepared using three polymer sheets.

FIG. 2A, a top view, illustrates one embodiment of the invention, a sealed package made from polymer films, containing two reactive precursor compartments, and one mixing and storage compartment. The storage compartment contains a sachet of fluid absorptive particles. FIG. 2B, a top view, illustrates another embodiment of the invention, a sealed package made from transparent polymer films, containing two reactive precursor compartments, and one mixing and storage compartment. The storage compartment contains an absorbent material useful for treating surfaces through wiping, scrubbing, or combinations thereof. FIG. 2C, a side view, illustrates another embodiment of the invention, a sealed package made from three polymer films, containing two reactive precursor compartments, and one mixing and storage compartment. The storage compartment contains an absorbent material useful for treating surfaces through wiping, scrubbing, or combinations thereof.

FIG. 9, a top view, illustrates one embodiment of the invention where two reactive precursor compartments are formed from a single compartment through use of an externally applied pressure mechanism such as a pressure clip or band. Removal of this clip or band creates a single mixing and storing compartment.

FIG. 10A, a top view, illustrates one embodiment of the invention, a sealed package made from two polymer films, with an adhesive backing which facilitates attachment to an object to a surface. FIG. 10B, a top view, illustrates one embodiment of the invention, a sealed package made from three polymer films, with an adhesive backing which facilitates attachment to an object to a surface.

FIG. 11, a to view, illustrates one embodiment of the invention, a sealed package made from polymer films, fitted with an external applicator useful in cleaning surfaces.

DETAILED DISCUSSION

Figure 3A:
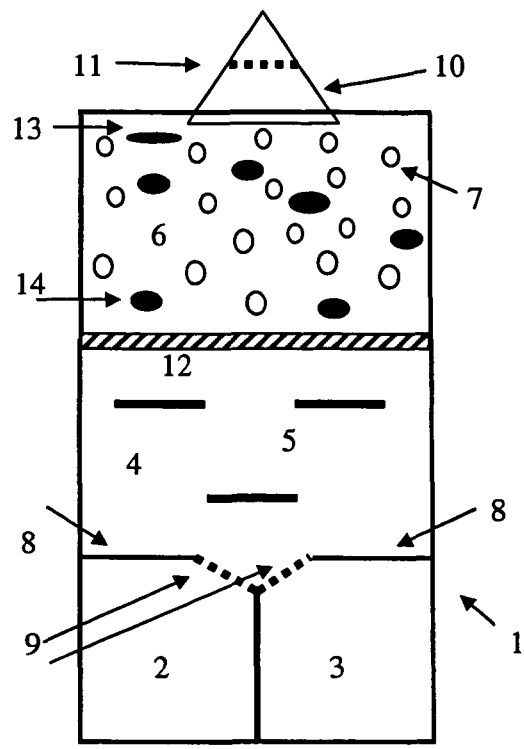
FIG. 3A, a top view, illustrates one embodiment of the invention, a sealed package made from transparent polymer films, containing two reactive precursor compartments, one mixing compartment, and one storage compartment. The device allows slow release of reactive gas from the compartment or rapid removal of gas, components, or a combinational thereof through a precision opening.

The invention disclosed involves the fabrication of devices which are used for the generation of reactive treatment agents and subsequent manipulation, and delivery of these agents from the device. Specifically, sealed packages contain compartments or chambers specialized for different functions. Compartments are designed for storage of reactive agent precursors, mixing of precursors, combining adjuncts, storage of the generated reactive treatment agents and adjuncts, and controlled delivery of the reactive treatment agents and optional adjuncts to a surrounding atmosphere, fluid, solution, porous or nonporous surface, or combinations thereof.

Manipulation of the materials inside the sealed package is accomplished by the use of internal or external pressurization of compartments and barriers sensitive to pressure, chemical reaction, or a combination thereof. Materials contained by the package are further manipulated through the association with particles, fibers, substrates, and combinations thereof that have the capacity to absorb and retain liquids. When liquids contain dissolved solids, suspended solids, gases, and combinations thereof, these agents also control these species. Use of absorbent materials in this manner further increases the safety of devices by minimizing liquid leakage.

Delivery of reactive treatment agents individually or formulated with solids, liquids, gases, or combinations thereof, is completed through the use of package design elements. In the case of gas delivery, gas release from the device can be controlled by using the porosity, permeability, and diffusion characteristics of device construction materials including coated and uncoated polymer films, as well as through predefined and controlled package openings, orifices, and fittings. Appropriately designed device openings can provide selective delivery of gas, liquid, solid, or combinations from the package. Device openings can be designed to be permanently open or to be resealed. Absorbent materials housed in the device or located external to the device may be used to apply the generated reactive agent to surfaces.

INDUSTRIAL APPLICABILITY AND GENERAL EMBODIMENTS

The devices of the invention facilitate the safe and economical generation of highly reactive treatment agents including high surface area solids, reactive liquids, reactive gases, and combinations thereof. Exemplary solids, in general, include instantly prepared adsorption materials including inorganic and organic precipitates and colloids, metals and metal chelates, and in combination with adjuncts. Exemplary liquids, in general, include water, aqueous solutions, solutions containing polar solvents, solutions containing dissolved and suspended species, nonpolar solvents, and solutions containing emulsions incorporating a wide range of chemical and biological agents, such as enzymes. Exemplary gases of the invention include chlorine dioxide, carbon dioxide, oxygen, sulfur dioxide, chlorine containing gases, and nitrogen containing gases. Exemplary reactive classes of molecules of the invention include oxidizing agents and reducing agents. Exemplary adjunct agents of the invention include solution modifiers, and those agents that provide feedback indicating remaining reactive agent and device lifetime as well as efficacy level. Preferred reactive treatment systems include complex mixtures of solids, liquids, gases and combinations thereof, where the liquids carry efficacious levels of reactive gases. Preferred substrates for delivering the reactive agents include woven and nonwoven materials and natural and synthetic porous materials.

The disclosed devices of the invention may be used to generate a wide range of different consumer, industrial, medical, and military products which provide significant utility. As example, a single one time use device can be prepared and utilized to complete the following operations: preparing a solution for treating, cleaning, sanitizing, and decontaminating porous and nonporous surfaces, purifying potable water, increasing the quality of recreational waters, treating laundry, and textiles, deodorizing and sanitizing breathing air, increasing the storage life of food and beverages, treating wounds and skin conditions, and preparing dietary supplements. A preferred agent for completing these operations is chlorine dioxide, and a preferred method of producing chlorine dioxide is the reaction of chlorine containing anions.

General embodiments include use of devices where the reactive precursors and materials used to prepare the reactive agents remain contained by the device, while the active agent is released to the surrounding liquid, gas, or surface application. General embodiments include the use of absorbent materials, particles, fibers, substrates, or combinations thereof inside these sealed devices to provide increased safety of operation, by minimizing loss of reactive precursors and treatment agents from the package which could occur during accidental breach of the device. General embodiments also include the controlled delivery of device contents after generation of the highly reactive treatment agent and in combination with soluble and insoluble adjuncts, and substrates. General embodiments include the saturation of objects contained in the enclosed system with active agents including woven and nonwoven materials, collections of particles, sponge-like materials, and fibers.

General embodiments involve the inclusion of devices and materials of the invention inside secondary packaging in order to treat an object and the enclosed space around the object. Preferred embodiments include food and medical supplies packaging. Further embodiments include methods and mechanisms for visualizing and monitoring the lifetime and remaining efficacy of devices and materials incorporated in devices, and utilizing simple power supplies to generate and control reactive agents. General embodiments include the preparation of devices and materials that can be attached to the outside of packages and containers which will eventually be stored in enclosed systems, for treating the atmosphere of the enclosure. General embodiments include use of the devices for preparation of health and wellness products and dietary supplements through precursor reactions that yield solids, liquids, gases, and combinations thereof. The mixing of these freshly prepared agents with previously prepared dietary supplements is a preferred embodiment.

Exemplary devices are inexpensive and minimize impact on the environment when needing disposal. The materials and devices of the invention have many unique properties and can be used in many operations that are recognized and approved by the USEPA, FDA, and USDA. As example, a preferred active treatment agent of the invention is chlorine dioxide. Laboratory studies indicate that chlorine dioxide is an exceptional biocide and highly efficacious at killing bacteria, fungi, molds, algae, protozoa, viruses and cysts. It is excellent in treating biofilms. It is useful as a sterilization gas at high concentrations. It is approved for operations including sterilizing manufacturing and laboratory equipment, bleaching pulp, paper, and textiles, washing fruit and vegetables, disinfecting flume water, disinfecting meat and poultry, disinfecting food processing equipment, sanitizing water, controlling odors in hospitals, petroleum industries, and animal feedlots and rendering operations, treating medical waste, treating municipal water, anthrax decontamination, and cleaning of electronic circuit boards.

Chlorine dioxide has been used to treat skin conditions, and wounds. Tissue inflammation in some cases may be treated. It has significant benefits in the treatment of recreational waters such as pool and spa water. New applications are being continually developed as this strong oxidizer is recognized as being a much safer and more selective reactant than chlorine. Likewise, carbon dioxide, sulfur dioxide, and chlorine dioxide as well as inert gases have significant utility in controlling chemical and biological contamination in liquids, at solid interfaces, and in the local atmosphere around packaged articles.

Beneficial Characteristics of the Invention:

Devices of the invention provide significant improvements in the safety, economics, and efficiency of generating, storing, and utilizing highly reactive treatment agents. Single and multiple use devices, which minimize disposal factors are easily prepared. Increased safety is obtained by preparing only the required amount of reactive agent for a specific operation and by preparing these agents in enclosed containers with controlled release designs. Specifically, handling and contact hazards for both precursors and treatment agents are minimized. Operator errors, which can be hazardous are reduced by controlling formulation parameters. When hazardous liquids, solids, gases or a combination thereof, are incorporated into devices, even greater safety can be obtained through incorporation of particles and fibers which allow control of liquid precursors, adjuncts, and generated reactive treatment agents. Preferred particles and fibers of the invention can both contain and retain, under pressure, solutions of highly concentrated reactive agent precursors and the generated reactive treatment agents. In doing so, devices that are damaged by puncture or other mechanisms will not leak liquids which are difficult to control. Additionally, particles, fibers, or combinations thereof containing solutions of known composition may be used to transfer known masses of active treatment agents including solids, liquids, and gases, to applications.

As example, reactive gases such as chlorine dioxide, sulfur dioxide, carbon dioxide, chlorine, and nitrogen containing gases, are commonly generated by mixing a caustic solution of anions with an acidic solution. This operation carries significant safety hazards to operators and bystanders. While using dilute solutions increases safety it limits the rate and quantity of gas production. Preparing these gases in a sealed enclosure utilizing specialized compartments and optional fluid control materials increases safety and can provide a convenient means of transporting and storing the reactive treatment agent until application.

Increased economy is realized by preparing only the instantly required amount of active treatment agent. Increased operations efficiency is realized by having the capacity to quickly and conveniently repeat this operation. Increased chemical reaction efficiencies associated with the generation of the treatment agent are obtained by increasing the concentrations of reactive agent precursors. Additionally, use of concentrated agents reduces packaging volume, decreasing both manufacturing and disposal costs.

Preparation of Materials and Devices of the Invention:

There are many methods of fabricating devices of the invention and practicing the invention using the combination of reactive precursor agents, fluid control agents, delivery substrates, and packaging design elements. Generally, an enclosed system or package is formed with polymer components, films, sheets, molded plastic components, or a combination thereof. In many cases, multiple films, laminated components, and substrate coatings are used to control gas and liquid containment properties. Reactive precursor agents are contained in individual compartments of the enclosed package. These compartments are of variable size and contain at least one pressure sensitive barrier each, which when breached allows passage of the precursor reagent into a storage compartment, mixing compartment, or combination thereof. Precursor reagents forms include solids, liquids, and liquids containing gases. Precursor liquids may range widely in viscosity and can incorporate fluid control agents such as absorptive particles, fibers, or a combination thereof. In general, at least one mixing or storage compartment or combination thereof, is present. This compartment can be initially present as a separate compartment or formed through the combination of two or more compartments. One or more compartments may also be unattached and mobile inside a larger package. Compartments can be formed by using integrated seals, barriers, or through the use of external pressure utilizing bands and clips. Precursor, mixing, and storage compartments can be designed in a wide variety of spatial orientations including in series, in parallel, side by side, face to face, or in stacked geometries.

Use of solid, liquid, and gas adjuncts allows complex formulations to be created. Compartments which isolate and protect adjunct materials from initial precursor reactions in some cases can aid formulation and device performance.

Exemplary packaging designs are disclosed in FIGS. 1-11 and include thin packages, double barrel cartridges, syringes, and cylinders with plungers. Those knowledgeable in the field will recognize the wide design parameters that are available while maintaining the principles disclosed herein. Materials contained in the enclosed system are moved between compartments as a result of externally applied pressures or internal pressure differences. Exemplary mechanisms include pressure and chemically sensitive barriers formed through chemical or thermal mechanisms. Exemplary materials used in fabrication of these enclosed systems allow long term storage of precursors and controlled manipulation of reactive treatment agents once formed. External pressurization of devices may be completed by using operator force such as the hands, manual plungers with integrated communication with package contents, and automated equipment which can apply pressure to devices. Exemplary designs also provide device lifetime information indicated through visual or electronic means.

In addition to precursor, mixing, and storage compartments, a wide variety of static mixing compartments can be included in series or parallel inside the enclosed package. Mixing compartments may utilize obstacles and impermeable barriers, holes or slots, which direct material flow and thus mixing. Additionally, these compartments can contain reactive agent precursors, adjuncts, or combinations thereof, as well as provide specialized delivery functions through use of materials with controlled porosity and diffusion characteristics. A large variation in the volumes of each compartment is possible, and optimum volumes are highly application specific.

Additionally, storage, mixing, or multiple function compartments can be fitted with electrodes and external contacts for connecting to a power supply. These components allow electrochemical processing of the precursor agents and the reactive treatment agents using simple power sources such as batteries and solar cells. The use of transparent films facilitates precursor processing with electromagnetic radiation.

Exemplary packaging materials include, thermoplastic elastomers such as polystyrene-diener, polyurethanes, copolyester-ethers. Exemplary materials include Bynel, Crystar, Dartek, Elvaloy, Delrin, polyethers of formaldehyde/ethylenoxide, polyethylene, polystyrenes, polyvinyl chlorides, ionomers, polyethylene terephthalates, polyvinyl acetates, polycarbonates, polyamides, polyvinyl alcohols, polyvinylidene chlorides, Ethylene acrylate copolymers including butyl-, ethyl- and methyl-acrylates (EBAs, EEAs and EMAs), nylons, celluloses, polypropylenes, polybutadienes and polyisoprenes, polyvinylchorides, propanediols, fluorinated polymers including Teflon, polyesters, Tyvek, and tyvek-type materials, Goretex and gortex type materials, laminated films, foil based films, clear foil laminations, metalized polyester-polyethylene laminations. Films can include clay coated papers and laminations. Exemplary packaging can be fully flexible, partially flexible, or rigid in construction, containing flexible components, rigid components, and combinations thereof.

Currently, various flexible packaging technologies use foil, metallized films, and high-barrier transparent films. Flexible food packaging films are preferred materials. These materials can provide optical transparency and moisture vapor transmission rates of less than 0.2 g/m2 day. Multilayer packaging constructions can provide a good combination of low moisture vapor transmission rates, high optical clarity, and good physical parameters. Combination of properties can be obtained by "sandwiching" different types of barrier films. These constructions can be produced using water-based coatings. Other exemplary materials from known manufacturers include SiOx-coated films, PVDC Latex (W. R. Grace), Ceramis (Alcan), Aclar (Honeywell), PET (Sheldahl), and PET (Dupont). Those experienced in the field will understand that material thickness is an important variable in package construction and that varying degrees of flexibility and handling are associated with each material type. Further, those experienced will understand the compatibility issues that exist between packaging components and the agents contained by the package.

Sealing of films and molded parts is accomplished through sonic welding, heat, adhesives, or the like. Compartments are generated through the use of pressure and chemical sensitive barriers generated with films and components of the device, where welding, heat, and adhesives are used to place barriers. Those experienced in the art will understand the temperatures and times associated with the sealing of packages and the types and varieties of high speed equipment available to form the packaging, load the packages, and seal the packages. Additionally, printing on the packages is common and those experienced in the art will understand the printing and labeling requirements associated with the different film and packaging materials as well as available equipment for completing the printing operation.

Preparation of Reactive Gases:

Gases are preferred reactive treatment agents of the invention. Exemplary reactive gases include chlorine dioxide, carbon dioxide sulfur dioxide, hydrogen sulfide, ammonia, chlorine gas, dichlorine monoxide, hydrocyanic acid, nitrogen dioxide, nitrogen oxide, hydrogen, nitrogen, and oxygen. Mixtures of gases may be simultaneously generated and contained by the materials and devices of the invention.

Exemplary gases can be prepared from simple and complex salts. In preparing the materials of the invention, the gas precursor reagents can be utilized in dry powder form, dissolved in a solvent, or when applicable, in a gaseous state. Liquids may be used prior to, during, or after gas generation. Detailed descriptions of suitable gas precursor reagents and methods for preparing examples of the reactive gases of the invention are provided herein.

Chlorine dioxide can be generated from solutions that contain the anion chlorite and an associated counter ion. Suitable chlorite sources include, alkali metal chlorites, such as sodium, lithium, and potassium chlorites, alkaline earth chlorites such as calcium and magnesium chlorite, chlorite salts of transition metals, chlorite salts of primary, secondary, and tertiary amines including ammonium chlorite, trialkylammonium chlorite and quaternary ammonium chlorite. Those skilled in the art will recognize that other chlorite salts are possible and the final application of the material will determine the optimum precursor species. Exemplary chlorite salts are those based on alkali metals.

Chlorine dioxide may also be generated using chlorate anions and an associated counter ion. Suitable chlorate sources include, alkali metal chlorates, such as sodium, lithium, and potassium chlorates, alkaline earth chlorates such as calcium and magnesium chlorate, chlorate salts of transition metals, chlorate salts of primary, secondary, and tertiary amines including ammonium chlorate, trialkylammonium chlorate and quaternary ammonium chlorate. Those skilled in the art will recognize that other chlorate salts are possible and the final application of the material will determine the optimum precursor species. Exemplary chlorate salts are those based on alkali metals.

Carbon dioxide gas is generated from solutions that contain the anions carbonate and bicarbonate and an associated counter ion. Suitable salts of these anions include alkali metal bicarbonates including sodium bicarbonate, potassium bicarbonate, and lithium bicarbonate, alkaline earth metal bicarbonates and carbonates, including calcium bicarbonate and calcium carbonate and magnesium bicarbonate and magnesium carbonate, bicarbonates and carbonates of primary secondary, tertiary and quaternary amines such as ammonium bicarbonate. A wide range of transition metal bicarbonates and carbonates may be used. Those skilled in the art will recognize that carbonate and bicarbonate are anions whose concentrations are also controlled in solution by adjustment of solution pH. Those skilled in the art will also recognize that many cationic polymer functionalities can provide the anions. Exemplary anions for generating carbon dioxide are the alkali metal bicarbonates.

Sulfur containing gases, such as sulfur dioxide and hydrogen sulfide can be generated from solutions that contain the anions sulfite, bisulfite and sulfide and an associated counter ion. Suitable sulfite and bisulfite salts include alkali metals salts of bisulfite and sulfite including sodium, potassium, and lithium, alkali earth metal bisulfites and sulfites, such as calcium and magnesium bisulfite and sulfite, and transition metal bisulfites and sulfites. Charged primary, secondary, tertiary, and quaternary amines of sulfites and bisulfites can be used. Suitable sulfide salts include alkali metals salts of sulfide including sodium, potassium, and lithium, alkali earth metal sulfides such as calcium and magnesium sulfides, and transition metal sulfides. Charged primary, secondary, tertiary, and quaternary amines of sulfides can be used. Those skilled in the art will also recognize that many cationic polymers can provide the anions. Those skilled in the art will recognize that sulfite, bisulfite, and sulfide are anions whose concentrations are also controlled in solution by adjustment of solution pH. Those skilled in the art will also recognize that many cationic polymer functionalities can provide the anions. Exemplary salts for generating sulfur containing gases such as sulfur dioxide and hydrogen sulfide are the alkali metal sulfites, bisulfites, and sulfides.

Nitrogen containing gases including nitrogen, nitrogen dioxide, and nitrogen oxide can be generated from solutions that contain the anions nitrate and nitrite and an associated counter ion. Suitable salts of these anions include alkali metal nitrites and nitrates including sodium, potassium, lithium nitrite and nitrate, alkaline earth metal nitrites and nitrates, including calcium nitrite and nitrate and magnesium nitrite and nitrate and nitrites and nitrates of primary secondary, tertiary and quaternary amines such as ammonium nitrite and ammonium nitrate. A wide range of transition metal nitrites and nitrates may be used. Those skilled in the art will recognize that nitrite and nitrate are anions whose concentrations are also controlled in solution by adjustment of oxidation reduction potentials. Those skilled in the art will also recognize that many cationic polymer functionalities can provide the anions. Exemplary salts for generating nitrogen gases are the alkali metal nitrites.

Chlorine containing gases including chlorine and chlorine monoxide can be generated from solutions that contain the anion hypochlorite and an associated counter ion. Suitable salts of this anion include alkali metal hypochlorites including sodium, potassium, and lithium hypochlorite, alkaline earth metal hypochlorites, including calcium and magnesium hypochlorite and hypochlorites of primary secondary, tertiary and quaternary amines. A wide range of transition metal hypochlorites may be used. Those skilled in the art will recognize that hypochlorite anion concentrations are also controlled in solution by adjustment of solution pH. Those skilled in the art will also recognize that many cationic polymer functionalities can provide the anions. Stabilized hypochlorite/hypochlorous acid solutions may also be used. Exemplary salts for generating chlorine containing gases are the alkali metal hypochlorites.

Cyanide gas can be generated from solutions that contain the cyanide anion and a counter ion. Suitable salts of this anion include alkali metal cyanides including sodium, potassium, and lithium cyanide, alkaline earth metal cyanides, including calcium and magnesium cyanide and cyanides of primary secondary, tertiary and quaternary amines. A wide range of transition metal cyanides may be used. Those skilled in the art will recognize that cyanide anion concentrations are also controlled in solution by adjustment of solution pH. Those skilled in the art will also recognize that many cationic polymer functionalities can provide the anions. Exemplary salts for generating cyanide gases are the alkali metal cyanides.

Precursors for generating oxygen gas includes peroxides or compounds generating peroxides, including organic or inorganic peroxides, peracids, or persalts. Preferred agents include hydrogen peroxide, peracetic acid, and monoperoxysulfate. A number of peroxides, peracids, and persalts have been disclosed by Fong in U.S. Pat. No. 4,964,870. This disclosure is incorporated in its entirety by reference.

Acids Used to Generate Gases:

Many exemplary reactive gases of the invention including chlorine dioxide, carbon dioxide, and sulfur and nitrogen containing gases can be generated by exposure of the gas precursor anions to acidic liquids, gases, or a combination thereof. Acids and more particular hydronium ions or protons can be provided by a wide range of chemical agents and through the presence of degradable chemical agents. Acid generating agents include water, protonated solvents such as alcohols, organic acids and inorganic acids. Acid provided by organic agents include, carboxylic acids, examples include acetic acids and naturally occurring acids. Both tartaric and citric acids are excellent agents for generating the reactive gases. Acid provided by organic agents also include, esters, anhydrides, acyl halides, carboxylates of polyhydroxyalcohols, degradable polyesters including polylactic acid, polyglycolic acid, polyacrylic acid and copolymers, polyacrylamide and copolymers, poly-beta-hydroxybutyrate, polylactone, anhydride or phosphate esters blended with or grafted to polypropylene, polyethylene, or polystyrene.

Acid anhydrides include organic acid anhydrides, mixed organic ahydrides, homopolymers of organic acid anhydrides, mixed inorganic acid anhydrides, copolymers of organic acid anhydrides, and mixed organic acid anhydrides containing conjugation. Exemplary anhydrides include polymers containing anhydrides including, maleic anhydride, methacrylic anhydride, acetic anhydride, propionic anhydride, succininc anhydride, vinyl, styrene, or alkene containing polymers, as well as polymers including esters of lactic and glycolic acid monomers.

Many polymers, copolymers, and grafted polymers are capable of providing hydronium ions and protons for gas generation. Exemplary polymers include xanthum gum, polyvinylpyrrooidone, polyvinylalcohols, polyanhydrides, polyacrylamides, lactic acid based polymers, glycolic polymers, hydroxyl acids, and mixtures thereof. Those experienced in the art will recognize that the amount of polymer-sourced acid provided to a system is based upon polymer molecular weight, amount of polymer present, and solubility characteristics of the different chemical species.

Inorganic chemical species and chemical agents that contain halides, phosphorus, silicon, sulfur and boron are excellent sources of acid for generating gases of this invention. Mineral acids, including hydrofluoric, hydrochloric, hydrosulfuric, hydrobromic, hydroiodic, phosphoric, boric, and silic acid are exemplary. The materials of the invention can use a wide concentration range of these acids including commercially available concentrates. Additional inorganic acid providing chemical species include, phosphate esters, trialkylsilylphosphate, sulfonic acid esters, sulfonic acid chlorides, phosphosilicates, phosphosilicate anhydrides, phosphosiloxanes, tetraalkyl ammonium phosphates, monobasic phosphates based on alkali metals, polymetaphosphates based upon alkali metals, borophosphates, aluminophosphates, silicophosphates, polyphosphates such as sodium and potassium tripolyphosphate, and mixed tripolyphosphates. Particulate metals and metal oxides can provide acid in order to generate gases of the invention. Oxides based upon aluminum, iron, silicon, and transition metals are applicable. Suitable salts for generating acid include metal salts such as iron chloride, iron sulfate, zinc sulfate, zinc chloride, cobalt sulfate, cobalt chloride, manganese sulfate, manganese chloride, copper sulfate, copper chloride, and magnesium sulfate.

Bases Used to Inhibit Gas Formation:

Materials of the invention can use chemical agents to control, stabilize, or inhibit the generation of gases. These methods are well understood in the field. As example, technical grade sodium chlorite is formulated with approximately twenty percent carbonate and sulfate species. The formulation yields a strongly alkaline pH upon dissolution. Alkaline pH solutions containing chlorite minimize the generation of chlorine dioxide gas. Bases and chemical species capable of reacting with acid compounds through neutralization of hydronium ions or accepting protons serve as a mechanism for inhibiting the reaction of acids with the anion precursors to the gases of the invention. Exemplary chemical agents include caustics prepared with alkali metals including sodium, potassium, and lithium hydroxides, as well as alkaline earth hydroxides such as calcium and magnesium hydroxides. Amines such as ammonia and ammonium hydroxide have acid neutralization capacity as do bicarbonates, carbonates, phosphates, sulfates, borates, and the salts of organic weak acids such as acetates. Those skilled in the art will recognize the wide range of acid neutralization chemical which are available. Additionally, acid base neutralization reactions can generate heat which allows the system temperature to be increased, controlling the delivery of gases external to the device.

Oxidizing Agents for Gas Formation:

Chlorine dioxide gas can be generated through oxidation with chemical agents or through electrochemical reaction. Exemplary agents include chlorine based oxidizers. Suitable chlorine containing species include chlorine gas, hypochlorites based on alkali salts and alkali earth salts. Stabilized chlorine species using cyanuric acid are also useful oxidizing agents.

Reduction Agents Used to Inhibit Gas Formation

Compounds that neutralize these oxidizing agents including chlorine based oxidizing agents inhibit the generation of chlorine dioxide gas. Exemplary neutralizing agents include bisulfites, thiosulfates, sulfites, reduced metals, and activated carbons. Additionally, increased system temperatures are obtained through oxidation and reduction reactions. Controlling system temperature provides greater control of reactive treatment agent generation and delivery, as well as application performance.

Adjuncts

The preparation of multi-component formulations containing a reactive treatment agent is a preferred embodiment. Many gas, liquid, and surface treatment applications are more easily accomplished by using the reactive treatment agent in combination with other agents which modify solution parameters or provide an additional surface treatment function. These additional agents are referred to herein as adjuncts. Many of the same adjuncts can be used in different applications and thus are included in a wide range of formulas. As example, many of the same minerals used in surface cleaning applications can be used as mineral supplements for nutritional or dietary improvement. Additionally, the type and concentration of adjuncts present in a formulation can have a significant impact on the form and solubility characteristics of active treatment agents. As example, reactive gas solubility can be affected by both temperature and dissolved solids.

Cleaning refers generally to a chemical, physical, enzymatic process, or combinations thereof for reducing or removing chemical or biological materials considers contaminants in or on the matrix that is under going the cleaning treatment. Adjuncts are widely available materials in solid, liquid, and gaseous form, with preferred species as solids, liquids or combinations thereof. The following are useful adjuncts for treatment and cleaning operations.

Oxidizing agents include hypohalite species and species which generate hypohalites, including alkali metal and alkaline earth salts of hypohalites, haloamines, haloimines, haloimides, and haloamides. Hypochlorite and hypobromite species are preferred. Preferred hypohalite species include sodium, potassium, lithium, calcium, and magnesium hypochlorite, chlorinated trisodium phosphate dodecahydrate, potassium and sodium dichloroisocyanurate and trichlorocyanuric acid. Organic hypohalite sources include, sodium and potassium salts of n-bromo and n-chloro imides, such as trichlorocyanuric acid, tribromocyanuric acid, dibromocyanric acid, dichlorocyanuric acid, and n-brominated and n-chlororinated succinimide, malonimide, pthalimide, and naphthalimide. Also, oxidizing agents including hydantoins are suitable for use in the invention. Preferred hydantoins include dibromo and dichloro dimethyl-hydantoin, n-chlorosulfamnide (haloamide) and chloramines (haloamine). Exemplary oxidizing agents also include peroxides, peracids, percarbonates, persulfates, and the reactive gases as described and including chlorine, chlorine dioxide, ozone, sulfur dioxide, and oxygen.

Heat Generation and Reducing Agents

Reducing agents can be any agent that reacts with an oxidizing agent or that leaves a material in a reduced state. Reducing agents can be utilized in many applications to treat unwanted or excessive concentrations of oxidizing agents and to modify metal species. Reducing agents can also be formulated directly with oxidizing agents for controlling treatment parameters. When both reducing and oxidizing agents are present at the same time, their reaction, generates heat. This heat is utilized to increase the efficiency of the cleaning operation as well as to manipulate the solubility of gases associated with liquids of the invention. As example mixing an excess of oxidizing agent with a reducing agent can increase material temperatures more than ten degrees Fahrenheit and often more than twenty degrees Fahrenheit. Exemplary materials include thiosulfates, bisulfites, and sulfites, with preferred agents used in alkali forms. Exemplary reducing agents include agents that react with hypohalites to generate heat, including reducing sugars, sulfur containing compounds, such as sulfite and bisulfite, thio-compounds such as thioureas. Additional compounds include borohydrides, hydrazine, and hypophosphite. Additionally, common heating mixtures involving the oxidation of metals are appropriate. A preferred metal is iron in the form of particles, filings, or shavings and in combination with carbons, and natural cellulose materials. Generation of heat provides several beneficial characteristics to the invention. In one example, the solubility of gases in liquids is reduced as the temperature of the liquid increases. Therefore, by using methods which increase the internal temperature of the device, gas can be driven from liquids contained by devices. This is useful for treating atmospheres and liquids surrounding devices that have low temperatures. Another example involves use of elevated temperature treatment agents to clean surfaces. Increasing the temperature of a cleaning formula can aid in increasing reactions with contaminants and in some cases melting and dissolution of contaminants.

Electrolytes

Salts which serve as electrolytes, and buffers may be included many different formulations. These adjuncts include carbonates, phosphates, pyrophosphate, aminocarboxylates, polycarboxylates, polyacrylates, phosphonates, amino phosphonates, polyphosphonates, and salts thereof, and combinations thereof. These agents may be used to control or modify the pH of solutions contained in the devices, and to manipulate the reaction of precursor compounds.

Viscosity

Viscosity modification agents include thickeners and rheology modifiers. Exemplary agents include natural polymers and gums, synthetic, polymers, copolymers of the like, glycerols, polyethylene glycols, and combinations thereof. Many suitable agents are commonly available including polyacrylates and modified acrylates, polyethylene-imine, xanthan gum, guar, Whelan gum. Thickeners can also be mineral based and include natural of synthetic clays such as smectic clays, hectoliter, aluminosilicates, expanded silica, attapulgite, and combinations thereof. Additional useful polymers adjuncts include methyl celluloses. Exemplary agents include hydroxyalkylcelluloses including hydroxylpropylmethyl cellulose and carboxymethyl cellulose.

Thickeners

A preferred agent includes binary surfactant viscoelastic thickener consisting of a betaine and an anionic counterion. Exemplary agents include alkyl betaines, alkylsulfobetaines, cetyldimethyl betaine (CEDB), alkoamido betaine, alkylamino betaine. Those experienced in the art will recognize that different molecular weight distributions are possible and that these distributions have characteristically different properties. Additionally, those experienced in the art will understand that saturated and unsaturated species are possible and this parameter affects solution characteristics. Preferred agents are fully saturated. Organic counter ions associated with the betaines include, alkyl carboxylates, aryl carboxylates, alkly sulfonates, aryl sulfonates, sulfated alkyl alcohols, sulfated aryl alcohols, and combinations thereof. These compounds can be substituted with commonly used functional groups including alkoxy, hydroxy, halogens, and nitro groups. The stability of these compounds and substituted compounds is impacted by other solution components including the concentration of hypohalites.

Foam Manipulation

Foam inhibitors include, silicone materials, fragrance oils, glycol ethers, and combinations thereof. Exemplary inhibitors include alkylated polysiloxanes including those that contain different functional groups including alkyls, aryls, and combinations thereof. Exemplary silanes include, dimethyl siloxane, diethylsiloxane, dipropylsiloxane, dibutylsiloxane, methylethyl polysiloxanes, phenylmethyl polysiloxanes, and combinations thereof. Additional exemplary agents include glycol ethers and ethylene glycol, n-hexyl ether, ethylene glycol n-butyl ether, dipropylene glycol methyl ether, dipropylene glycol n-butylether, propylene glycol n-butyl ether, propylene glycol n-propyl ether and combinations thereof. A preferred agent is dipropylene n-butyl ether. Foam stabilizers may be used including celluloses, alkylcelluloses, hydroxyalkylcelluloses as example hydroxyethylcellulose, and combinations thereof.

Organic Solvents

Organic solvents that can be used include alcohols, such as methanol, ethanol, and propanol, and amines. Exemplary amines include alcohol based amines such as ethanolamine. Hydrotropes may be used including alkali metal salts of aromatic sulfonates. Exemplary agents include, sodium xylene sulfonate, sodium butyl monoglycol sulfate, sodium toluene sulfonate, sodium cumene sulfonate, and combinations thereof. Many solvents with a wide miscibility in water are available and include hydrocarbons, ketones, aldehydes, carboxylic esters, terpenes, glycol ethers, and combinations thereof. Those experienced in the art will understand compatibility requirements between solvents and polymer packaging materials.

Additional Adjuncts

Devices and materials described herein can take advantage of a wide range of adjuncts. Some formulations can be used in many different applications while some formulations are highly specific for niche applications. Adjuncts that are exemplary include acids, bases, solvents, enzymes, surfactants, detergents, foaming agents, foam inhibitors, cyclodextrins, resorcinol, resorcinol derivatives, and combinations thereof. Enzymes include lysins, lipases, keratinases, proteases, amylases, cellulases, enzymes targeting chemical and biological weapon agents, and combinations thereof. Surfactants and detergents include species which are cationic, anionic, zwitterionic, amphoteric, nonionic, and combinations thereof. Fragrances, dyes, and corrosion inhibitors are also exemplary. Exemplary bases include, phosphates, carbonates, bicarbonates, sesquicarbonates, and combinations thereof, alkali salts of carbonates, bicarbonates, and sesquicarbonates, alkaline earth salts of carbonates, bicarbonates, and sesquicarbonates, and combinations thereof. Exemplary acids include, inorganic acids such as sulfuric, hydrochloric, phosphoric, nitric, boric, and organic acids such as formic, acetic, malic, succinic, tartaric, lactic, glutaric, glycolic, fumaric, benzoic, citric, sulfamic, oxalic, and combinations thereof. Exemplary agents also include soluble metals, chelating agents such as EDTA and amino acids, metal ligands including amines, biocides including quaternary amines, organic acids such as fatty acids, micelles, and emulsions. Many biological components including DNA, RNA, proteins, peptides, and associated molecules are applicable. Exemplary biological agents include, enzymes, protein fragments, and emulsions or micelles that contain these agents. Additional exemplary agents include, odor neutralizing agents, odor masking agents, disinfecting agents, preservatives, biocides, bacteriostats, fungistats, osmostic regulators, sequestering agents, pesticides, insecticides, herbicides, pheromones, and animal attractants. Those skilled in the art will recognize that combinations of certain soluble, suspended, and reactive agents are not compatible and will neutralize or generate undesirable or unwanted chemical species.

In some cases dissolution of adjunct agents or dilution of highly concentrated adjuncts can provide a mechanism for increasing system temperatures. Increasing system temperature affects solubility, and treatment performance of many formulation components and mixtures.

Suspended Adjuncts:

Devices and materials can incorporate particulate matter including colloids and nanoparticles. When liquids are present these liquids can also carry colloids and nanoparticulate material in suspension. Particles with nanometer sizes can contain surface reactive chemicals such as metal ions and organic functionalities which are highly reactive with both chemical and biological contaminants. Those experienced in the art will understand that aggregation between particles is very common and that solution parameters greatly affect aggregate formation and sizes. Preferred suspended materials include naturally occurring, and synthetic minerals, resins, and polymers. Exemplary materials include metals, alloys, metal oxides, insoluble minerals, and combinations thereof.

Synthetic and natural fibers can be prepared in nanometer to hundreds of nanometers length species. Suitable materials include those that are used to prepare current larger dimension fibers including, cotton, wool, polypropylene, rayon, polyester, nylon, acrylic and many others. Additional exemplary organic polymers are described below.

Non-Suspended Particles

Particulate and fiber materials too large to be suspended are also highly useful in many embodiments described herein.

Those skilled in the art will recognize that surface wetting and liquid transfer between and on different particles types can occur, and this transfer can modify the surface and pore properties of each particle type. Those skilled in the art will also recognize that materials that carry liquids containing reactive agents may be incompatible with certain additional particle types. As example materials of the invention that contain the gas carbon dioxide will have significant gas concentration loses when mixed with caustic particles such as carbonates and magnesium oxides. Both particulate and fiber form are acceptable for the embodiments described herein.

Preferred and applicable materials include naturally occurring, synthetic, and recycled materials. Exemplary materials include desiccants, amorphous silicates, zeolites, metal oxides and hydroxides, reduced metals, phosphates, and carbonates.

Catalytic materials based on metals and enzymes are quite common and these are applicable in all known forms. Those experienced in the art will recognize that the deposition of molecules containing active sites that include metals and atoms and nanocomposites of metals and semimetals on the surface of support materials are immediately applicable as formula components.

A preferred material is polycarbonate. It has been observed that polycarbonate has a significant capacity for storing and releasing chlorine dioxide. Polycarbonate can contain concentrations of chlorine dioxide great enough to yield a colored material. When exposed to solutions of high concentrations of chlorine dioxide yellow colored polycarbonate objects are obtained. The gas contained by the carbonate can be released over time and is available for the applications described herein. Flushing of the gas and solvent from polycarbonate can be observed by the loss of color. This preferred material is used commonly in eyewear, the medical and surgical field, and to produce objects with high impact resistance. The unique interaction of polycarbonate with chlorine dioxide facilitates the design and application of high impact objects that possess the capacity to control chemical and biological contaminants at their surface.

Synthetic and natural fibers, including strings, yarns and textiles including, cotton, wool, polypropylene, rayon, polyester, nylon, acrylic are also applicable in formulations. Ion exchange material is a preferred material and includes resins selected from functionalized styrenes, vinylchlorides, divinyl benzenes, methacrylates, acrylates, or mixtures, copolymers, and blends thereof. Natural and synthetic zeolites such as clinoptilolite and glauconate are preferred.

Particulate and fiber material whether suspended or not suspended can have a wide range of sizes and size distributions. Nanometer and micron size particles may be suspended while useful particles in the size range between 10 microns and 10 millimeters are not normally suspended but mixed with the liquids contained by the devices. Particulate and fiber materials with absorption and adsorption properties will have dynamic sizes, controlled by the amount and types of fluids present. Particle morphology has been shown to be important in cleaning operations, providing varying degrees of abrasive properties, and surface areas. Those experienced in the art will understand the relationship between particle size, morphology, composition, and abrasive characteristics. Additionally, aggregates of all particle types are possible and that both particulate composition and solution parameters affect aggregation.

Dietary Supplements:

A preferred embodiment is the instant preparation of dietary supplements and formulation of these supplements with additional nutraceuticals and botanicals. Preferred materials include phosphates of alkali, alkaline earth and transition metals, carbonates of alkali, alkaline earth and transition metals, sulfates of alkali, alkaline earth and transition metals, chlorides of alkali, alkaline earth and transition metals, chelates of alkali, alkaline earth and transition metals, chlorine dioxide, aminoacid metal chelates, nitrogen containing chelates for metals, citric acid chelates, vitamins, nutritional minerals including silicates, carbonates, phosphates and combinations thereof, animal and plant material extracts including fruits, vegetables, and components of fruits and vegetables. Preferred materials also include probiotics, enzymes, prebiotics, and symbiotics. These materials may be initially loaded into devices in stable dormant forms and activated through proper combinations of ingredients. Those experienced in the art will recognize that some of these agents are incompatible and must be separated and that many of these species have varying degrees of solubility in water. Further many of these compounds and preparations are sensitive to pH, electrolyte strength and temperature. Furthermore bioavailability is highly controlled by formulations and compositions. Even further many of these materials can be used in a fashion to indicate to the user of the device that the preparation is ready for ingestion. This information can be obtained by visual changes, temperature changes and viscosity changes in materials. Preferred mechanisms include modifications in color and transparency, increased temperature, and increases or decreases in solution viscosity. Those experienced in the field understand that different colors may be used, and combinations of feedback mechanisms may be utilized together. Further those experienced will understand the effects of temperature and radiation, and that stability of these systems can be varied and tuned in many ways.

Fluid Control Adjuncts:

Adjuncts that can control fluids through adsorption and absorbance are advantageous in maximizing the safety and utility of many devices and embodiments described herein. Materials that can retain fluids even under increased pressure are preferred for many embodiments which involve the delivery of reactive gases without the bulk exchange of liquid. Exemplary fluid control materials include absorbent polymers and minerals. These materials may be in the form of particles, fibers, or combinations thereof, and they may be used to control reactive precursors, reactive agents, adjuncts, or combinations thereof. Exemplary delivery materials also include materials in the form of porous films, sheets, membranes, and combinations thereof. In many instances controlling fluids allows the gases and suspended solids to also be controlled.

The absorbent particles and fibers can be obtained from a variety of natural and synthetic sources and can consist of organic materials, inorganic materials, or combinations thereof. Further, the absorbent materials may be homogeneous or heterogeneous in distribution of the different synthetic, natural, organic, or inorganic components. Those familiar with the technology and art of absorbency also understand that adsorption occurs at the surface of these materials and that both molecular scale and bulk scale solvent and solute interactions can occur in simultaneous and continuous fashion. Additionally, those experienced in the art of preparing absorbent materials understand that nonwoven, woven, and combinations thereof, physically and chemically treated fibers as well as wrapping and layering of sheets of similar and dissimilar materials has considerable impact on material functional properties.

Absorbent materials suitable for the invention include sponges, foams, and absorbent minerals and polymers. These materials may be in the form of particles, fibers, or combinations thereof. Foams and sponge materials can hold and contain liquids in widely varying amounts based upon preparation methods. Sponge materials can be naturally occurring or synthetic. Applicable materials include polyethers, polyesters, polyurethanes, celluloses, polyethylenes, polyvinylalcohols, corks, and butyl rubbers and copolymers of the different species. Pore and cell type, open or closed, and size can be modified to change absorption properties. Foam materials can be further treated to be fire retardant, flexible, or semirigid. Manufacturing methods such as reticulation also effect absorbency. Additionally woven and non-woven materials have the capacity to adsorb and absorb fluids. The type of fluids and capacity of uptake are dependent upon fiber types, manufacturing methods and surface treatment. Foams, sponges, and fiber absorbents carry chemical compatibility characteristics related to their composition and method of manufacture. Those skilled in the art will recognize and understand the chemical compatibility requirements of the different materials.

Exemplary polymer based materials are stable in contact with highly caustic solutions of metal chlorites, and chlorate solutions, in concentrated acids, and in the presence of high concentrations of reactive gases including chlorine dioxide, carbon dioxide, and gases containing nitrogen, oxygen, and sulfur. As example, caustic solutions of sodium chlorite are known to be stable for long periods of time in superabsorbent polymers prepared with acrylic acid and with acrylamide. Likewise, concentrated hydrochloric acid solutions are stable for long periods of time. Similarly, absorbent articles that are stable with reactive agent precursors including anions, bases, cations and acids are suitable materials. Exemplary inorganic materials include smectic type minerals. Inorganic sources of liquid carrying and absorbent particles include aluminosilicates, smectic or montmorillinite clays, and a preferred materials including, bentonite, attipulgite, and expanded silica.

Preferred and applicable absorbent material for absorption of fluids of the invention and may be generated from a range of synthetic and natural polymer materials. The class of materials known as "superabsorbents" is particularly suitable in this regard. Superabsorbents are natural, synthetic, or mixed polymers that are not fully cross-linked. They may be classified as polyelectrolyte or nonpolyelectrolyte types as well covalent, ionic, or physical gelling materials. These materials have the capacity to absorb many times their own volume in fluid. Examples of synthetic materials include polyacrylic acids, polyacrylamides, poly-alcohols, polyamines, and polyethylene oxides. The composite superabsorbent material may also be selected from derivatives of polyacrylic acids, polyacrylamides, poly-alcohols, polyamines, polyethylene oxides, cellulose, chitins, gelatins. starch, polyvinyl alcohols and polyacrylic acid, polyacrylonitrile, carboxymethyl cellulose, alginic acids, carrageenans isolated from seaweeds, polysaccharides, pectins, xanthans, poly-(diallyldimethylammonium chloride), poly-vinylpyridine, poly-vinylbenzyltrimethyl ammonium salts, polyvinylacetates, polylactic acids, or combinations thereof. The composite material may also comprises a material selected from resins obtained by polymerizing derivatives of acrylic acid or resins obtained by polymerizing derivatives of acrylamide.

Biodegradable materials that are suitable include cellulose derivatives, chitins, and gelatins. Additionally mixtures of synthetic polymer and natural polymers either as distinct chains or in copolymers may be used to generate these absorbent materials. Examples include starch polyacrylic acid, polyvinyl alcohols and polyacrylic acid, starch and polyacrylonitrile, carboxymethyl cellulose, alginic acids carrageenans isolated from seaweeds, polysaccharides, pectins, xanthans, poly(diallyldimethyl ammonium chloride), polyvinylpyridine, polyvinylbenzyltrimethyl ammonium salts, cellulose, alginic acids, carrageenans isolated from seaweeds, polysaccharides, pectins, xanthans, starch, or combinations thereof, polyethyleneglycol, a polylactic acid, a polyvinylalcohol, a co-polylactideglycolide, cellulose, alginic acids, carrageenans isolated from seaweeds, polysaccharides, pectins, xanthans, and starch.

As those experienced in the art will understand the process of cross-linking polymer chains derived from either sole source or combinations of sources, are variable and will affect the magnitude of fluid absorption, and the types of fluids that may be absorbed. Additionally those experienced in the art will understand that molecular characteristics such as polymer chain composition, functional group position and distribution as well as polymer molecular weight and distribution will effect performance, and will know how to modify these parameters to vary the properties of the resulting composite consistent with the basic tenets of the invention. Further those experienced in the art will understand that the volume capacity of a material is also subject to the type and composition of the fluid in which the material is exposed. Furthermore, the crosslinks and polymer backbones may be disrupted by reactive agents including oxidizing agents. In some embodiments these systems can be formulated to contain high concentrations of oxidizing agents for a short period of time and then to breakdown yielding only a reactive fluid.

Non-Particulate Materials:

Non-particulate materials or substrates are highly useful for spreading and wiping cleaning agents on a surface, dislodging and disrupting surface contaminants, and for holding the removed contaminants. Substrates for wiping surfaces, are well known in the art and include woven substrates, non-woven substrates, hydroentangled substrates, sponges, and combinations thereof. Multiple layers may be present and the two sides of the wipe material may be similar or different. Different textures may be present providing different wet strengths, abrasivity, loft, and porosity. Exemplary materials include cellulose wadding of different grades, polypropylene needle punched material, combinations of cellulose and synthetic fibers. Synthetic fibers can include rayons, polyesters, polypropylene and the like. Mechanical treatments can include needle-punching, hydroelongation, and hydroentanglement. When multiple layers are used they may be assembled through common methods including but not limited to needle-punching, chemical bonding, sewing, thermal bonding, sonic bonding, and combinations thereof. Preferred materials also include silicone sheets.

Coating of Non-Soluble Adjuncts

Those experienced in the art will also understand that particulate, fiber, and substrate materials of the invention, whether used as fluid control, reactive agent delivery, or as an adjunct material may be surface modified with a range of compounds and through different binding methods. Preferred surface modifications yield cationic surface functionalities. Examples of preferred surface modification chemicals include chemical agents selected from 3-acryloxypropylotrichlorosilane, 3-acrlyoxypropylotrimethocysilane, Allyltrichlorosilane, allyltrimethoxysilane, allyltriethoxy silane, 3-bromopropylotrichlorosilane, 3-bromopropyl-trimethoxysilane, (p-chloromethyl) phenyltrichlorosilane), (p-chloromethyl)phenyltrimethoxysilane, 1-trimethoxysilyl-2-2(p, m-chloromethyl)-phenylethane, chloromethyltrichlorosilane, chloromethyltriethoxysilane, 2-chloroethyltriethoxysilane, 3-chloropropyltrichlorosilane, 3-chloropropyl-trimethoxysilane, 3-glycidoxypropyltrimethoxysilane, 3-iodopropyl trimethoxysilane, 3-isocyanatopropyltriethoxy silane, 2-(diphenylphosphino) ethyltriethoxysilane, vinyltriacetoxysilane, vinyltrichlorosilane, vinyltriethoxysilane, vinyltrimethoxysilane, 3-mercaptopropyltrimethoxysilane, 3-mercaptopropyltriethoxysilane, N-(triethoxysilylpropyl) urea, 3-aminopropyl-triethoxysilane, 3-aminopropyltrimethoxy silane, N-(2-aminoethyl)-3-aminopropyltrimethoxysilane, 2-(carbomethoxy) ethyltrichlorosilane, N-[(3-trimethoxysilyl)propyl] ethylenediamine triacetic acid, trisodium salt, 3-cyanopropyltrichlorosilane, 3-cyanopropyltriethoxysilane, 2-(4-chlorosulfonylphenyl) ethyltrichlorosilane, 2-(4-chlorosulfonylphenyl) ethyltrimethoxysilane, 2-(trimethoxysilyl) ethyl-2-pyridine, N-(3-trimethoxysilylpropyl)pyrrole, N-octadecyldimethyl-1(3-trimethoxysilyl)propyl]ammoniumchloride, N-trimethoxysilylpropyl-n,n,n-trimethyl ammoniym chloride, 3-(trimethoxysilyl)propyldimethyloctadecylammonium chloride silane quaternary amine, chloropropyl trihydroxy silane, polyamines, polyamides, polyalcohols, polysaacharides, polyacrylamides, polyacrylates, humic acids, peptides, proteins, polorganozirconates, polyorganoaluminates, polysiloxanes, polysilanes, polysilazanes, polycarbosilanes, polyborosilanes, zirconium dimethacrulate, zirconium tetramethacrylate, zirconium 2-ethylhexanoate, aluminum butoxides, aluminum diisopropoxide ethylacetoacetate, tetramethyldisiloxanes and derivatives thereof, tristrimethylsilylphosphate and tristrimethylsiloxyboron, polyamines such as poly(DADMAC), poly-DADM, polyamine-poly(DADMAC) blends, polyquartenary amines, inorganic-polyamine blends, and inorganic poly(DADMAC) blends, cationic starch, cationic poly-methylmethacrylates, copolymers of vinylimidazolium methochloride and vinylpyrrolidone, quarternized vinylpyrrolidone/dimethylaminoethyl-methacrylate copolymer, polyethyleneimine, or combinations thereof.

Additionally, surface binding methods that provide the capacity of immobilizing biological material, proteins, peptides, antibodies, and pharmaceutical agents are preferred means of modifying the surfaces of non-dissolved materials. Those experienced in the art will recognize that numerous procedures exist for generating stable surface coatings of these materials.

DETAILED DESCRIPTION OF FIGURES

In general devices can be prepared with two or more films. When using two films, pressure, chemical or a combination of the like sensitive barriers are prepared using both the top and bottom films. Two or more compartments optimized for specific purposes such as chemical precursor storage, mixing, reaction product storage, or chemical release may be prepared. These compartments may be organized in many different spatial geometries and orientations, such as face to face, side by side, and stacked. Those experienced in the art will recognize the advantages associated with storing, mixing, and delivering the chemical species of the invention using different and optimized compartments. When using more than two films, pressure, chemical or a combination of the like sensitive barriers can be prepared using intermediate or "middle" films, or a combination of top, bottom and intermediate films. Optimized compartments for chemical precursor storage, mixing, reaction product storage, or chemical release can be prepared in multiple geometries and in multiple combinations. An exemplary device design involves the use of three films. Using three films multiple chemical precursor storage compartments, mixing and reaction product storage compartments can be generated. Device designs using three films can efficiently utilize a single barrier film for generation of two chemical precursor storage compartments. In general the chemical or pressure sensitive barriers may be placed in wide variety of orientations and with widely varying dimensions. Those experienced in the art will understand the advantages to different size barriers as well as the placement of barriers for storing, mixing, moving, and delivering agents of the invention.

FIG. 1.

FIG. 1A, top view, illustrates one embodiment of the invention, an enclosed package (device) made from two polymer films which are thermally sealed around the periphery, (1). This device contains two reactive precursor storage compartments (2 and 3), each prepared with permanent barriers (8) and pressure sensitive barriers (9). These pressure sensitive barriers are prepared through thermal or chemical methods using the top and bottom film of the package. These reactive precursor storage compartments are situated side by side. The device has one mixing and product storage compartment (4) which is in direct communication with the reactive precursor storage compartments. Storage compartment (4) contains optional absorbent particles, fibers, or a combination thereof (5). A design element also prepared with polymer film (6), with integrated mounting hole (7) is provided for hanging or mounting the device. The mounting element may also be prepared with molded components, adhesive, Velcro or the like. Package contents available after reaction can be delivered from the package by cutting or tearing the package. Additionally, gas phase products may escape from the package by diffusion through the polymer films, controlled porosity of the package, or combinations thereof.

FIG. 1B, a side view, illustrates a related design to that presented in FIG. 1A except that the device is prepared with three polymer films.

Here the device is thermally sealed around the periphery (1). Reactive precursor storage compartments (2,3) are prepared using the package's top film, bottom film and intermediate film (8). The intermediate film (8) serves as a common permanent barrier wall for the two reactive precursor storage compartments. In the design presented, the intermediate film does not extend the full length of the mixing and product storage compartment (4). In this design, pressure sensitive barriers created using thermal, chemical, or a combination of the like interactions, are fabricated using the top and intermediate film and the bottom and intermediate film. The reactive chemical precursor storage compartments are thus organized as a stack. Storage compartment (4) contains optional absorbent particles, fibers, or a combination thereof (5). A design element also prepared with polymer film (6), with integrated mounting hole (7) is provided for hanging or mounting the device. The mounting element may also be prepared with molded components. Package contents available after reaction can be delivered from the package by cutting or tearing the package. Additionally, gas phase products may escape from the package by diffusion through the polymer films, controlled porosity of the package, or combinations thereof.

The devices depicted in embodiments 1A and 1B are suitable for preparing materials which can be applied as disinfectants, odor control agents, decontamination and fumigation agents, gas and air treatment materials, respiratory agents, food and beverage processing and preparation agents, nutritional supplement generation, manipulation, and delivery, chemical and biological neutralization agents, and for preparing solutions and substrates for porous and nonporous surface cleaning operations in many industrial, residential, medical, and military situations. Exemplary treatment agents that can be prepared include reactive gases such as chlorine dioxide, precipitates and colloids such as phosphates and carbonates, in combination with adjuncts such as thickeners and pH modifiers. When gases are generated, the gas can slowly escape from the package through film or device pores or diffusion through materials. For faster release of gas, removal of storage compartment contents, or combinations thereof, the storage compartment may be opened through cutting or tearing at a predefined locations. Devices may be generated in a wide range of sizes in order to treat small enclosures such as individual food containers, larger devices for treating refrigerators and small rooms, and even larger devices for treating shipping containers, ventilation systems and facilities. Small devices are also suitable for the instant preparation of fresh colloids and chelates for use as dietary and nutritional supplements.

FIG. 2A, 2B, 2C:

FIG. 2A, top view, illustrates one embodiment of the invention, an enclosed package (device) made from two polymer films which are thermally sealed around the periphery, (1). This device contains two reactive precursor storage compartments (2 and 3), each prepared with permanent barriers (8) and pressure sensitive barriers (9). These barriers are prepared through thermal or chemical methods using the top and bottom films of the package. The reactive precursor storage compartments are situated side by side. The device has one mixing and reaction product storage compartment (4) which is in direct communication with the reactive precursor storage compartments. Storage compartment (4) contains an optional sachet (6) or sachets of absorbent particles, fibers, or a combination thereof (5). A design element (7) is provided for hanging or mounting the sachet and is in the form of a string, fiber, or filament. The sachet may be used by removal from the external package (1) or used in place by opening the external package (1) through cutting or tearing at defined locations.

FIG. 2B, top view, illustrates one embodiment of the invention, an enclosed package (device) made from two polymer films which are thermally sealed around the periphery, (1). This device contains two reactive precursor storage compartments (2 and 3), each prepared with permanent barriers (8) and pressure sensitive barriers (9). These barriers are prepared through thermal or chemical methods using the top and bottom films of the package. These precursor storage compartments are situated side by side. The device has one mixing and reaction product storage compartment (4) which is in direct communication with the reactive precursor storage compartments. Storage compartment (4) contains a wipe or multiple wipes (10) fabricated with woven, nonwoven, or a combination of the like material. The wipe or wipes may be used by removal from the external package (1) or used in place by opening the external package (1) through cutting or tearing at defined locations.

FIG. 2C, side view, illustrates one embodiment of the invention, an enclosed package (device) made from three polymer films which are thermally sealed along the periphery (1). Those experienced in the art will recognize that devices of this kind can be prepared using multiple polymer films or from folding and manipulating one or more single polymer films. This device contains two chemical precursor storage compartments (2 and 3) separated by a permanent barrier wall (8). Pressure sensitive barriers (9) are prepared through thermal or chemical mechanisms between the device's outer film and the barrier film (8). External pressure applied to the chemical storage compartments through hand pressure (squeezing, rolling, or the like) or mechanical pressure causes the pressure sensitive barrier to rupture and solution to flow out of the compartments. Those experienced in the art will recognize that the pressure sensitive barrier can be tuned to a broad range of sensitivities. The chemical precursor storage compartments (2 and 3) are in direct communication with the mixing and reaction product storage compartment (4). The product storage compartment (4) contains a nonwoven, woven, or combination thereof wipe or wipes (10) capable of absorbing all or part of the fluid entering this compartment (4). The wipe or wipes may be used by removal from the external package (1) or used in place by opening the external package (1) through cutting or tearing at defined locations.

Devices illustrated in FIGS. 2A, 2B, 2C can be used for delivery of reactive agents to liquids gases, and surfaces by either removing the sachet or wipe from the package or by opening the outer package and allowing the reactive agents to escape. Solid surfaces may be treated by removing the sachet or wipe and directly applying to a porous or nonporous surface.

FIG. 3A:

FIG. 3A, top view, illustrates one embodiment of the invention, an enclosed package made from two polymer films which are thermally sealed along the periphery, (1). The device contains two reactive precursor storage compartments (2 and 3), each fabricated with fixed barriers (8) and pressure sensitive barriers (9). Reagent precursors exiting the storage compartments enter a mixing compartment (4) fabricated with mixing elements (5). Mixing elements are prepared by chemically or thermally sealing package films. In this device chemical reagents, solids, liquids, gases, or a combination thereof can exit the mixing compartment (4) and enter a reaction product storage or delivery compartment (6). Optional pressure sensitive barrier (12) or barriers can be used to separate compartments (4) and (6). Storage compartment (6) can also contain optional absorbent particles, fibers, or a combination thereof (7), optional minerals (14) and optional dietary or nutritional supplement materials (13). A precision material delivery element (10) prepared in a predefined location (11) with a defined or variable orifice allows package contents to be delivered with varying levels of control. This opening may also be fabricated using molded components which are integrated into the films of the device.

FIG. 3B

Figure 3B:
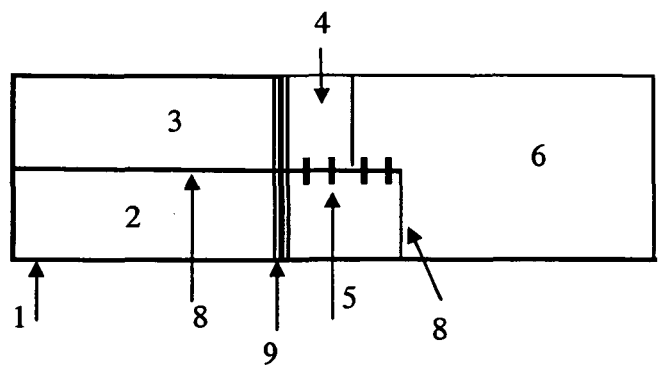
FIG. 3B, a side view, illustrates one embodiment of the invention, a sealed package made from three polymer films, containing two reactive precursor compartments, one mixing compartment, and one storage compartment. The device allows slow release of reactive gas from the storage compartment or rapid removal of gas, components, or a combinational thereof through a precision opening.

FIG. 3B, a side view, illustrates one embodiment of the invention, an enclosed package made from three polymer films which are thermally sealed along the periphery, (1). The device contains two reactive precursor storage compartments (2 and 3), each fabricated with a common fixed barrier (8) and pressure sensitive barrier (9). Reaction precursors exiting the storage compartments enter a mixing compartment (4) fabricated with mixing elements (5). Mixing elements are prepared by chemically or thermally sealing the outer films with the intermediate film as well as providing holes for transport of chemical species. This mixing compartment can have a wide range of mixing elements/holes with different sizes, shapes, and spatial locations. The dimensions of the mixing compartment can vary widely and can also be utilized as a product storage compartment. In this device, chemical species, solids, liquids, gases, or a combination thereof can exit the mixing compartment (4) and enter a product storage or delivery compartment (6). Storage compartment (6) can contain optional absorbent particles, fibers, or a combination thereof (7), optional minerals (14) and optional dietary supplement materials (13). A precision material delivery element (10) is provided in a predefined location (11) that allows the device to have a orifice for the controlled delivery of package contents. Molded parts may also be implemented for further controlled delivery of package contents. Elements 7, 14, 13, 10, and 11 are omitted for clarity.

Devices and derivatives of these devices as illustrated in embodiments 3A and 3B are suitable for preparing materials which can be applied as disinfectants, odor control agents, decontamination and fumigation agents, gas and air treatment materials, respiratory agents, food and beverage processing and preparation agents, nutritional supplement generation and manipulation, chemical and biological neutralization agents, and for preparing solutions and substrates for porous and nonporous surface cleaning operations in many industrial, residential, medical, and military situations. Exemplary treatment agents that can be prepared include reactive gases such as chlorine dioxide, oxidizing agents such as hypochlorite, precipitates and colloids such as phosphates and carbonates, in combination with adjuncts such as thickeners and pH modifiers. When gases are generated, the gas can slowly escape from the package through controlled film or package pores or diffusion through package materials. For faster release of gas, removal of storage compartment contents, or combinations thereof, the package may be opened through cutting or tearing at predefined locations. Devices are suitable for instantly fabricating fresh colloids and chelates, activating enzymes and microorganisms, and for preparing dietary and nutritional supplements. Those experienced in the art will understand that different polymer films, thickness, and surface treatments can modify the release characteristics of package contents. Additionally, different films can be used for construction of the different compartments of these devices in order to further optimize the function of each compartment. As example low gas permeable films can be used for reactive precursor storage compartments and higher gas permeable films can be used for fabrication of the reaction product delivery compartment.

Figure 4:
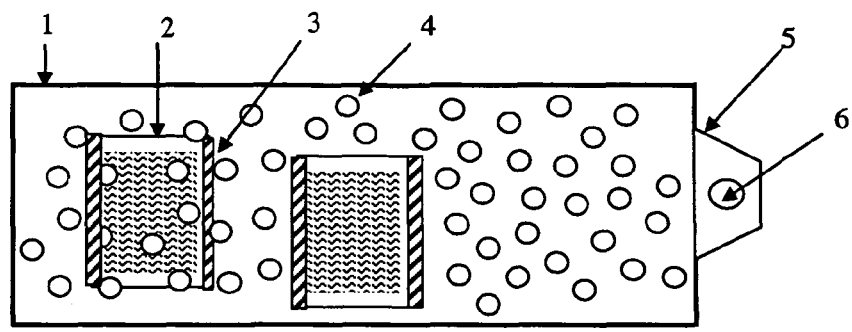
FIG. 4, a top view, illustrates one embodiment of the invention, a sealed package made from polymer films, containing two reactive precursor compartments which are freely mobile in the primary package.

FIG. 4:

FIG. 4, top view, illustrates one embodiment of the invention, an enclosed package made from transparent polymer films which are thermally sealed along the periphery, (1). This device contains two reactive precursor compartments (2) which are freely mobile in the package. The reactive precursor compartments (2) are prepared by thermally sealing polymer films with one or more pressure sensitive seals (3) prepared through chemical or thermal mechanisms. Preferred designs utilize more than one pressure sensitive seals. Also freely moving in the main package (1) are optional absorbent particles, fibers, or combinations thereof (4) which in this embodiment carry a reactive chemical precursor. Reactive precursors contained in compartments (2) and absorbent particles, fibers, or combinations thereof (4) react to yield gases, precipitates, colloids as well as indicators useful visualizing package contents, readiness for use status, and remaining lifetime. The device package (1) is fitted with a mounting element (5) containing a mounting hole (6). When gases are generated with the device, the gas can slowly escape from the package through controlled film or package pores or diffusion through package materials. For faster release of gas, removal of storage compartment contents, or combinations thereof, the package may be opened through cutting or tearing at predefined locations.

Figure 5:
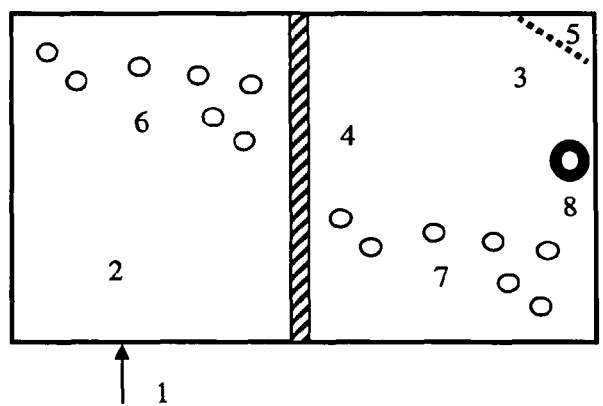
FIG. 5, a top view, illustrates one embodiment of the invention, a sealed package made from transparent polymer films, containing two reactive precursor compartments, and a single pressure sensitive barrier which allows communication of materials between the two compartments.

FIG. 5:

FIG. 5, top view, illustrates one embodiment of the invention, an enclosed device made from polymer films which are thermally sealed along the periphery, (1). One or more of the films may be transparent to allow visualization of package contents. This package contains two reactive precursor compartments (2 and 3). The reactive precursor compartments (2 and 3) are separated by a single pressure sensitive barrier (4) prepared by thermal or chemical mechanisms. After the barrier (4) is breached a single mixing and storage compartment is generated. A predefined package opening element (5) is included and designed to be cut or torn to allow removal of package contents. An optional mounting hole (8) allow the device to be hung from a string, fiber, wire, filament, or similar element. Compartments (2 and 3) contain reactive precursors (6) and (7) which may be carried by optional absorbent particles, fibers, mats of fibers, or combinations thereof. Those experienced in the art will understand that the films used to fabricate each compartment can be of different composition, thickness, or surface coating or a combination of the like in order to optimize the device for a specific purpose or function. As example, one compartment can be prepared to have a low gas permeability while the other compartment can have a greater gas permeability.

Figure 6:
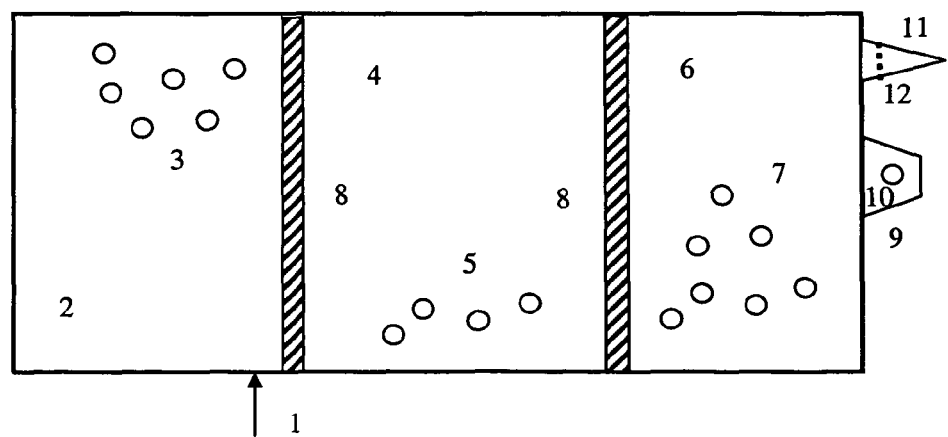
FIG. 6, a top view, illustrates one embodiment of the invention, and is similar to the embodiment diagrammed in FIG. 5, but with the exception that an additional compartment is provided with pressure sensitive barrier.

FIG. 6:

FIG. 6, top view, illustrates one embodiment of the invention, an enclosed package made from transparent polymer films which are thermally sealed along the periphery, (1). This package contains two reactive precursor compartments (2 and 6), and a mixing and reaction product storage compartment (4). Reactive precursor storage compartments (2 and 3) communicate directly with the mixing and reaction product storage compartment (4) with pressure sensitive barriers (8). The pressure sensitive barriers created through chemical, thermal, of combination thereof mechanisms, can be or various dimensions and orientations. Preferred designs allow the contents of each compartment to easily be transferred in their entirety to other compartments. Optional reagent and absorbent particles (3, 5, and 7) are housed respectively in compartments (2, 6, and 4). Package (1) contains both a mounting element (9) with mounting hole (10) as well as a predefined precision delivery element (12). Elements for delivery of package contents (12) can function through cutting or tearing. Molded components may also be incorporated into the device for delivery of the package contents. Those experienced in the art will understand that the films used to fabricate each compartment can be of different composition, thickness, or surface coating or a combination of the like in order to optimize the final device for a specific purpose. As example, one compartment can be prepared to have a low gas permeability while the other compartment can have a greater gas permeability.

Figures 7A, 7B:
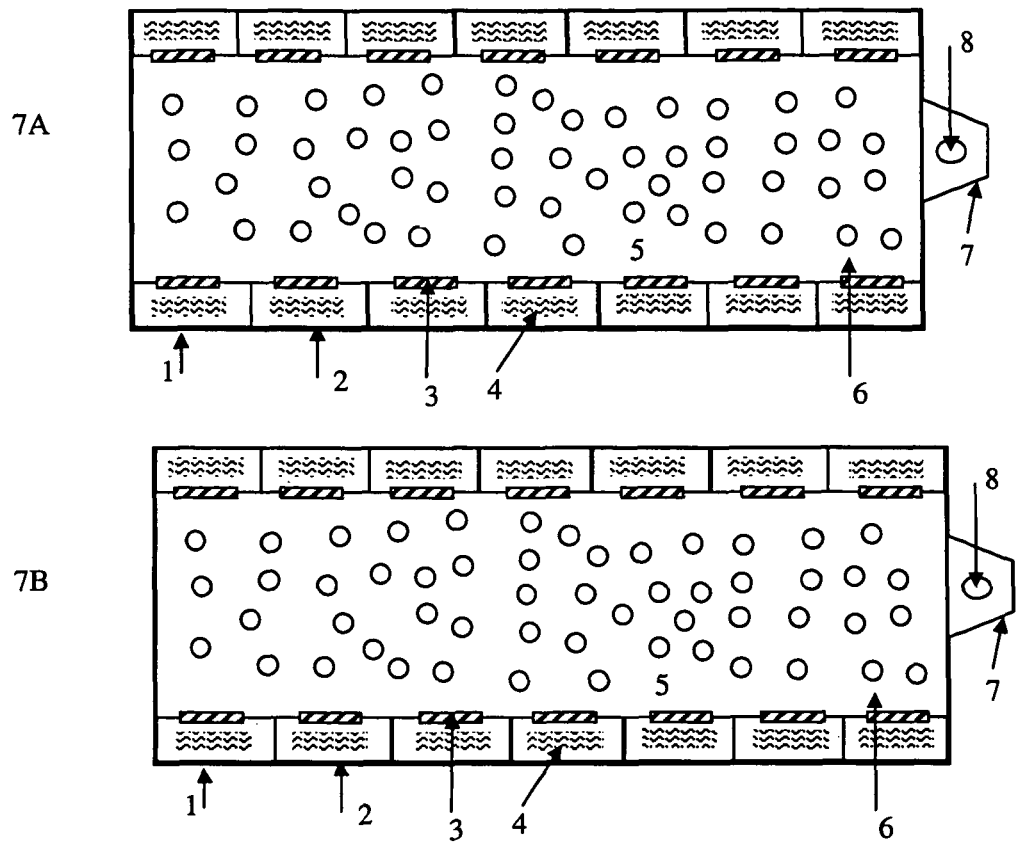
FIG. 7A, a top view, illustrates one embodiment of the invention, a sealed package made from a polymer films, containing fourteen reactive precursor sub-compartments, and one mixing-storage compartment, containing particles with a reactive precursor. The device is designed for generating fourteen separate reactive solution-gas charges.
FIG. 7B, a top view, illustrates one embodiment of the invention, a sealed package made from a polymer films, containing twenty eight reactive precursor sub-compartments, in a stacked arrangement, and one mixing-storage compartment, containing mixing holes. The device is designed for generating twenty eight separate reactive solution-gas charges.

FIG. 7A:

FIG. 7A, top view, illustrates one embodiment of the invention, an enclosed package made from two transparent polymer films which are thermally sealed around the periphery, (1). This package contains fourteen reactive precursor storage compartments (2), and a mixing and storage compartment (5), which contains optional absorbent particles, fibers, or a combination thereof, and optionally containing a reactive precursor agent (6). Each of the fourteen precursor storage compartments (2) communicate with the mixing and storage compartment (5) with a pressure sensitive barrier (3), and contain a reactive precursor agent (4). The device (1) contains both a mounting element (7) with mounting hole (8). This device can be used to generate a single daily charge of reactive treatment agent for two weeks. Those experienced in the art will understand that the films used to fabricate each compartment can be of different composition, thickness, or surface coating or a combination of the like in order to optimize the final device for a specific purpose. As example, one compartment can be prepared to have a low gas permeability while the other compartment can have a greater gas permeability.

FIG. 7B:

FIG. 7B, top view, illustrates one embodiment of the invention, an enclosed package made from three transparent polymer films which are thermally sealed around the periphery, (1). This package contains twenty-eight reactive precursor storage compartments (2). These reactive precursor storage compartments are stacked two-deep, one under the other. A mixing and reaction product storage compartment (5), is centered in the package, and contains optional absorbent particles, fibers, or a combination thereof, and optionally containing a reactive precursor agent. Particles, fibers, chemical species are omitted for clarity. The intermediate film contains mixing and transport holes (6) in the mixing and reaction product storage compartment (5). Each of the twenty-eight precursor storage compartments (2) communicate with the mixing and storage compartment (5) with a pressure sensitive barrier (3), and contain a reactive precursor agent (4). Pressure sensitive barriers can be prepared in a wide variety of dimensions and orientations. The device (1) contains both a mounting element (7) with mounting hole (8). This device can be used to generate a single daily charge of reactive treatment agent for twenty eight days. Those experienced in the art will understand that the films used to fabricate each compartment can be of different composition, thickness, or surface coating or a combination of the like in order to optimize the final device for a specific purpose. As example, one compartment can be prepared to have a low gas permeability while the other compartment can have a greater gas permeability.

Figures 8A, 8B:
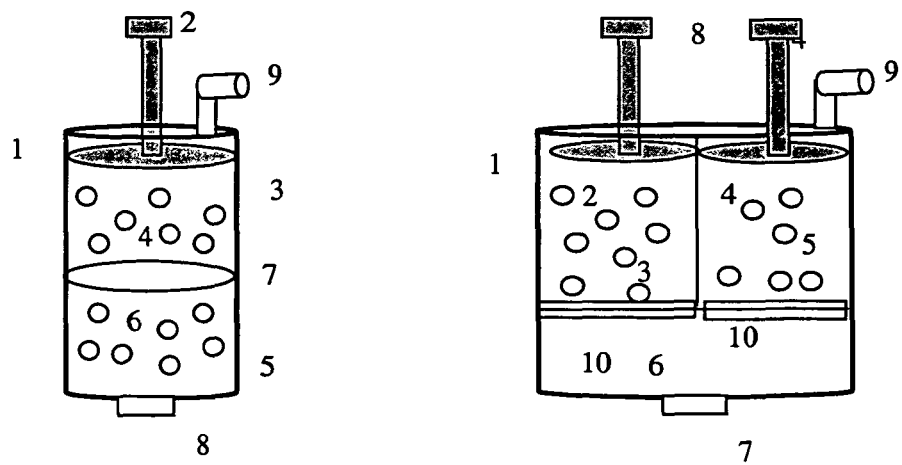
FIG. 8A illustrates one embodiment of the invention, a sealed molded package in the shape of a barrel.
FIG. 8b illustrates another embodiment of the invention with two barrels, and one mixing storage compartment.

FIG. 8A illustrates one embodiment of the invention, a sealed molded package (1) in the shape of a barrel with a plunger (2). On a small scale the device is a syringe on a larger scale the device is a drum (1) and plunger (2). The barrel contains a barrier seal (7), prepared through chemical, thermal, or a combination thereof mechanism, which is pressure sensitive and serves to separate two reactive precursors (4 and 6) in compartments (3 and 5). Upon breach of the seal (7), by pushing down on the plunger (2), the precursors (4 and 6) react. The device is designed to allow slow release of the gas through a connection or membrane (9) or to release the package contents through element (8). The plunger (2) may contain design elements such as holes and slits that are useful for mixing and communicating container materials to different locations inside the container. FIG. 8b illustrates one embodiment of the invention, which is similar to that described in FIG. 8A, but with two side-by-side barrels (1), and one mixing storage compartment (6) which communicates directly with reactive precursor compartments (2 and 4). Reactive precursors (3 and 5), are moved through pressure sensitive openings (10) in order to initiate reactions. On a small scale the device (1) is a syringe on a larger scale the device is a portioned drum and two plungers (2). Upon breach of the seals (10) the precursors (3 and 5) react and the device is designed to allow slow release of the gas through a connection or membrane (9) or to deliver the contents through design element opening (7). The plungers (2) may contain holes, slits, and design elements that facilitate mixing and communication of materials throughout the container.

FIG. 9:

FIG. 9, top view, illustrates one embodiment of the invention, an enclosed package made from transparent polymer films which are thermally sealed around the periphery, (1). This device contains two reactive precursor compartments (2 and 4). The reactive precursor compartments (2 and 4) are separated by a single clip (6) which eliminates communication of materials between compartments (2 and 4) by pressure. Compartments (2 and 4) contain reactive precursors (3 and 5) which may be in the form of reactive precursor containing particles, fibers or combinations thereof. Reactive precursors contact, mix and react only after the clip (6) is removed. Removal of the pressure clip yields a single storage and mixing compartment. This device facilitates the simple preparation and delivery of reactive gases. Delivery of the active agents can be controlled through a combination of polymer film properties and precision device openings. Those experienced in the art will understand that the films used to fabricate each compartment can be of different composition, thickness, or coating or a combination of the like in order to optimize the final device for a specific purpose. As example, one compartment can be prepared to have a low gas permeability while the other compartment can have a greater gas permeability. The number and dimensions of these compartments and associated clips can vary widely.

FIG. 10A:

FIG. 10A, top view, illustrates one embodiment of the invention, a device (2) which attaches to a surface (1). This surface may be porous or nonporous and may be part of a container. This container may ultimately be stored in an enclosed space. The device (2) includes an adhesive or Velcro-type element on the underside, for permanently or temporarily mounting to the surface. The device (2) is designed to release a gaseous treatment agent into the atmosphere around a sealed object or a container. The release of the active treatment agent may be used for purposes of protecting the object it is packaged along side, or for treatment of the enclosed space where the package is placed. The device (2) is made from thermally sealing along the periphery, one or more transparent polymer films, containing two reactive precursor storage compartments (3 and 5); one in the optional shape of a circle (5). A single pressure sensitive barrier (7) provides communication of reactive materials (4 and 6) between the compartments. Reactive precursors may be carried by absorbent particles, fibers, or combinations thereof. Upon breaching the barrier (7) the precursor reagents react producing a reactive treatment agent such as a gas, which can slowly escape from the package (2) using the inherent film properties, controlled pores in the device, or a combination thereof. Different concentrations of reactive agents, as well as visual indicators can yield information associated with remaining device efficacy, exposure conditions of the container it is attached to and combinations thereof. Devices (2) can be both temperature and pressure sensitive and yield information associated with these parameters through visual means.

FIG. 10B:

FIG. 10B, top view, illustrates one embodiment of the invention, a device which attaches to a surface (1). This surface may be porous or nonporous and may be part of a container. This container may ultimately be stored in an enclosed space. The device (2) can carry an optional adhesive or Velcro-type backing for permanently or temporarily mounting to a surface. This device (2) may also be packaged along side another object without attachment to a surface. The device (2) is designed to release a gaseous treatment agent into the atmosphere around a sealed object or a container. The release of the active treatment agent may be used for purposes of protecting the object it is packaged along side, or for treatment of the enclosed space where the package is placed. This device (2) is prepared by thermally sealing along the periphery, three or more polymer films, containing two reactive precursor storage compartments (3 and 4), organized in a stacked geometry. Pressure sensitive barriers (8) allow communication between reactive precursor storage compartments and a mixing and reaction product storage compartment (5). Reactive precursors may be carried by absorbent particles, fibers, or combinations thereof. Upon breaching the barriers (8) the precursor reagents react producing a reactive treatment agent such as a gas (6), which can slowly escape from the package (2) using the inherent film properties, controlled pores in the device, or a combination thereof. Different concentrations of reactive agents, as well as visual indicators can yield information associated with remaining device efficacy, exposure conditions of the container it is attached to and combinations thereof. Devices (2) can be both temperature and pressure sensitive and yield information associated with these parameters through visual means.

FIG. 11:

FIG. 11, top view, illustrates one embodiment of the invention, a device prepared with an enclosed package constructed from three or more polymer films which are thermally sealed along the periphery, (1). The device contains two reactive precursor compartments (2 and 3), in a stacked geometry, each with a common permanent barrier (8), not shown, and a pressure sensitive barrier (9). One precursor mixing and reaction product storage compartment (4) which is in direct communication with the chemical precursor storage compartments. Product storage compartment (4) contains optional adjuncts (5) along with the generated treatment agent. A material delivery vehicle (6), communicates material to a solid surface cleaning element (7). The device (1) is attached to a polymer support (10) which has and integrated handle with optional grips (11) and mounting hole (12). The solid surface contactor (7) may also be housed on a polymer support (10). The device is suitable for cleaning porous and nonporous surfaces. Those experienced in the art will recognize that the design of the cleaning tool is highly variable with respect to the shape, dimensions, and materials of construction.

Specific Use Embodiments

In one embodiment devices of the invention are used to prepare reactive treatment agents for treating porous and nonporous surfaces, and porous and nonporous materials. These devices and materials are useful for many different residential cleaning operations including but not limited to, kitchen, bathrooms, automobiles, pet care, and recreational structures. These devices are also useful for surface cleaning in medical, industrial, and military applications. A preferred treatment agent is chlorine dioxide prepared by reacting sodium chlorite with an acid or by reacting sodium chlorite with sodium hypochlorite. Mixtures of chlorine dioxide and hypochlorite are useful in that different degrees of cleaning can be obtained. Both of these compounds are oxidizing agents with chlorine dioxide soluble in solution as a true gas. Both of these agents can be formulated with adjuncts. Preferred adjuncts include gelling agents such as acrylic acid and abrasive materials such as calcium carbonate. Adjuncts that control pH are useful in controlling the ratio of hypochlorous acid to hypochlorite. A preferred adjunct includes fluorinated polymers such as Teflon which aid in surface treatment. Chlorine dioxide and chlorine are two of the most potent biocides available and provide excellent control of biofilms. As a result, these devices are useful in preparing secondary solutions for decontamination surfaces in industrial, medical and military applications. The devices are useful for generating treatment agents for preparing of secondary solutions which can be utilized by mop and bucket, sprayers, hand applicators and the like.

In another embodiment devices of the invention are used to prepare materials for use in residential, industrial, medical, and military laundering applications. Materials containing reactive gases such as chlorine dioxide are useful in the washing process as well as in enclosed drying systems. Preferred devices are those that allow gas escape without bulk transfer of liquids and initial reactants. Devices may also be used for microbial control. Adjuncts that are useful include softening agents and static control agents used in drying operations. When used in the washing operation bulk liquid containing oxidizing gases can be formulated with detergents, ion binders, chelates, fragrances, fabric protectors, and many others. Chlorine dioxide is a preferred oxidizing agent having much greater reaction selectivity than bleach, resulting in more gentle care to clothing and fabrics. Similar application in textile treatment is possible.

In another embodiment, devices of the invention are used to generate materials and for treating local atmospheres, air flow equipment, filters, and baffles, and structures involved with ventilation systems, heating and cooling systems, and air recirculation systems. Chlorine dioxide is a preferred treatment agent as it has been demonstrated to be effective on many odor causing chemicals, microorganisms, and biofilms. It has been used for the decontamination of biological and chemical weapons including anthrax. Adjuncts useful in this embodiment, include air fresheners and humidity control agents. Devices are useful for treating residential heating and cooling systems, industrial HVAC systems, military systems including temporary shelters, and medical facilities. Industries with odor control problems include those involved with petroleum, wastewater, animal care and processing, and food processing.

In another embodiment devices of the invention are used to generate materials and for the sanitization, disinfection, sterilization and maintenance of clean conditions for instruments, equipment, and materials associated with hospital, medical, surgical, and dental use. Devices are useful in such applications where the device is included in the primary packaging of the object or subsequent repetitive treatment of equipment and instrumentation. Chlorine dioxide is a preferred agent and has been demonstrated to satisfy treatment requirements for many materials now used in the medical, surgical, and dental fields.

In another embodiment devices of the invention are used to generate materials for the simultaneous absorption and treatment of medical wastes. Preferred treatment agents include chlorine dioxide gas carried by a fluid absorbed by absorptive particles and fibers. Preferred absorptive polymers include super-absorbents based upon acrylic acid, acrylamide, or combinations thereof and celluloses. By utilizing an absorbent particle which is partially swollen with fluid containing chlorine dioxide, but with sufficient remaining absorbency, medical wastes, and unknown liquids can be absorbed, retained, and treated. Adjuncts useful in this embodiment include additional biocides including glutaraldehyde, surfactants, silver, surfactants, and polar solvents. Adjuncts that control pH are highly useful and include caustics such as alkali hydroxides, organic acids, and inorganic acids such as hydrochloric and sulfuric. Preferred agents include additional oxidizing agents such as persulfates, peroxides, percarbonates, and peracids. Medical wastes that can be treated include blood, urine, and bodily fluids associated with hospital, medical, and surgical treatment. Treatment of these fluids in this manner significantly reduces the hazards associated with transmission of disease.

In another embodiment materials devices of the invention are used to prepare materials for the treatment of wounds, sores, and skin conditions. Preferred treatment agents include chlorine dioxide, carbon dioxide, and oxygen and standard ointments, lotions, crèmes, and solution ingredients. These gases are able to penetrate deeper into wounds, sores, and skin tissue than topical ointments. Preferred devices include those that allow treatment gases to interact with the wound or sore while limiting direct contact with precursor reagents and devices, solutions, and systems that allow lotions, ointments, bandages and dressings to be loaded with active treatment agents immediately prior to use. Adjuncts include standard components lotions such as synthetic and natural polymers, hydrogels, hydrocolloids, and materials and compounds that provide protective barriers and protection of skin hydration and which increase skin hydration. Additional useful adjuncts include electrolytes, buffers, and silver salts. In some cases materials prepared in devices of this embodiment and associated with bandages allow the simultaneous control of exudates and delivery of active treatment agents.

In another embodiment devices of the invention are used to generate materials for personal hygiene and infant care. These devices can include wipes and absorbent products which are exposed to materials of the invention prior to use. Situations targeted include, diapers, incontinence, menstruation. Preferred treatment agents include chlorine dioxide, carbon dioxide, and oxygen and standard adjuncts. Preferred adjunct agents include odor control agents, fragrances, and absorptive cellulose based polymers. Preferred devices are those that allow gas to escape without bulk transfer of liquids and precursor agents. Additional adjuncts include lotions which provide and protect loss of skin moisture. In some instances, materials prepared allow both fluid control and treatment.

In another embodiment devices of the invention are used to generate materials for treating non-aqueous fluids such as fuels, lubricants, and cutting fluids, which contain water, biological, and chemical contaminants. In this embodiment absorbent polymers are utilized which contain chlorine dioxide gas and appropriate adjuncts such as hydrocarbon based biocides. Devices used in this embodiment can treat fuels by simultaneously removing water and releasing biological control agents. Additional chemical treatment can be performed by including adsorbents which effectively remove contaminants such as heavy metals and sulfur.

It another embodiment devices of the invention are used to generate materials that can simultaneous contain a chemical or biological military agent in liquid or powder form, neutralize, and breakdown these agents. In this embodiment absorbent polymers, activated inorganics and organics, foaming and thickening agents can be used. Additionally, pH modifiers are beneficial in increasing the rate of hydrolysis of specific agents. The use of substrates such as wipes prepared from woven and nonwoven materials are preferred agents for decontaminating and cleaning solid surfaces. These materials may be prepared in the enclosed systems or the materials of the devices removed from the devices and associated with the wiping substrate. Those experienced in the art will understand which agents require acidic pH treatment and which agents require alkaline pH treatment. Exemplary agents that can be treated include those of biological origin, and those chemicals that contain, sulfur, phosphorus, chlorine, and arsenic.

In another embodiment, devices and materials are prepared for improving the storage and transport of food and food products. Meat, poultry, and seafood are preferred food systems for improving storage. Juice and fluids from these foods must be controlled in sealed packages and thus absorbent materials are often incorporated into the packaging. Studies have shown that controlling liquid and limiting contact with the food, aids in the control of spoilage, and increases product lifetime. In this embodiment two different devices containing absorbent polymers can be used. The first incorporates a liquid permeable material containing absorbent particles and the precursors for chlorine dioxide. The absorbent particles and fibers contain additional capacity to absorb liquids from the food. When food fluids are absorbed by the particles chlorine dioxide is generated. This gas controls microorganism growth in the packaging materials, and also provides treatment of the atmosphere around the food in the sealed package, as well as on the surface of the food. The second preferred device includes those that allow gas escape without bulk transfer of liquids and initial reactants. Exemplary devices such as that diagrammed in FIGS. 10A and 10B allow gas to be released into the enclosed space and to associate with the food surface as well as the absorbent materials in contact with the food surface, which may or may not contain an additional treatment agent. This treatment can improve the storage lifetime and the quality of the food product. As temperature increases in the sealed container increased concentrations of chlorine dioxide are released into the atmosphere around the food, thus addressing the increase in microbial activity that occurs with increasing temperatures. Additionally, odor is controlled by reaction of chlorine dioxide with the odor causing compounds. This dynamic treatment system increases the safety of transporting food between refrigerated storage systems. Suitable adjuncts include cellulose polymers to increase absorption and fluid handling, woven and nonwoven materials, and food grade polymer films.

In another embodiment, devices of the invention are used to generate materials for treating recreational water systems, such as pools and spas for chemical and biological contaminants. These water systems utilize a range of chemicals including halogen based oxidizing agents, peroxide based oxidizing agents, surfactants, flocculating agents, biocides, pH control agents, alkalinity and hardness agents, and a wide range of specialized treatment agents for inorganic, organic, and microbiological contaminations. In this embodiment chlorine dioxide is used as a primary or secondary biocide for the water system. It can be used with any of the commonly used water treatment additives. A preferred combination of chlorine dioxide and hypochlorous acid allows a wide range of water systems to be treated. Devices in this embodiment are also exemplary for use with simple power sources such as batteries and solar cells. Using these simple power sources, chlorine dioxide can be generated through electrochemical reaction of a chlorite salt. A preferred chlorite salt is sodium chlorite. Preferred treatment adjuncts include treatment metals such as silver, copper, and zinc.

In another embodiment, devices with design elements that provide visual indicators for determining the remaining lifetime of a device are preferred. Devices that contain gases, minerals, and fluids with different pHs can provide visual indication of agent presence and remaining device or material efficacy. Preferred visualization agents include pH sensitive dyes, colored minerals, colored enzyme reaction products, and gas color. Preferred color agents are those that are approved for food and beverage use. Preferred gases include chlorine dioxide and carbon dioxide. Solutions of chlorine dioxide are colored in shades of light green, yellow, and brown depending upon concentration. Carbon dioxide concentrations can affect solution pH, which is then indicated by a pH sensitive indicator. Gas solubility in fluids is a function of temperature and pressure, as well as solutions composition. Devices that contain gases will respond to changes in temperature and pressure. As example devices that contain chlorine dioxide will rapidly lose contained gas, and thus color, when temperatures increase. This situation allows not only remaining lifetime of the device to be understood, but also indicates that the object, package, or the like that is associated with the device has been exposed to elevated temperatures or changes in pressure.

In another embodiment, materials and devices are prepared for inclusion, adherence, or combinations thereof, to packaged articles which will be stored in enclosed systems, such as refrigerators, freezers, coolers, and shipping containers. Refrigerators and enclosed spaces are prone to contamination and odor accumulation due to lack of air flow and treatment. By attaching a small device to an object, which will be stored, that contains an odor and contaminant treatment device, the enclosed space can be treated when the object is place into it. Exemplary systems include objects that are ultimately placed in enclosed refrigerated or freezer spaces. Preferred treatment agents are gases such as chlorine dioxide which treat both microbiological contamination including biofilms, and odor causing agents associated with food and beverage storage. Exemplary articles include beverage containers, cases, and specifically designed packaging for refrigerators and food items which are stored in refrigerators for extended periods of time including salad dressing, jellies, condiments, and pre-prepared foods. Devices of this embodiment also serve to indicate the date of when the object was placed in the enclosed space and the temperatures and pressures which it has been exposed.

In another embodiment devices and materials are prepared for activating and delivering viable organisms and their components. Preferred organisms include microorganisms including bacteria and algae. Additional biological species include animal cells, proteins, genetic material and enzymes. Many bacteria, algae, animal cells, and biologically active molecules are stored in a form that increases storage life. In many situations it is beneficial to activate or change the environment of these agents before delivery to the application. Exemplary applications include medical procedures, preparation of dietary supplements, plumbing and waste system treatment, military decontamination operations, and cleaning operations. Those experienced in the art will recognize that different activation environments are required for different agents. As example anaerobic organisms are ideally activated in anaerobic environments while aerobic organisms are ideally activated in environments that contain oxygen. Exemplary adjunct materials include minerals, resins, and polymers which provide surfaces for activation, and nutritional agents for utilization by propagating organisms and cells. In many situations the agent to be activated is located in a compartment isolated from precursor agents storage compartments.

In another embodiment devices of the invention are used to generate materials for treating potable water. Waters used for drinking, cooking and cleaning often contain microbiological and chemical contaminants. It is customary to treat these waters with a range of treatment agents including halogen based oxidizing agents. Preferred agents include chlorine dioxide and absorbent polymers. In some situations, it is beneficial to expose potable water to the gas chlorine dioxide without bulk mixing of the reagents used to generate the gas. Devices of this embodiment are preferred for completing this task. In use of these materials and devices in this manner, it may be advantageous to drive the generated gas from the device into the water to be treated. This can be accomplished by increasing the temperature of the liquid in the device through the use of reactions that generate heat. Preferred reactions include mixing of oxidizing and reducing agents, mixing or acids and bases, and use of metal oxidation reactions. Additionally, simple resistive or radiative heating can be used. Preparation of potable water often is a preliminary step for the production of beverages and thus this embodiment addresses the generation of beverages. Ideal adjuncts for creating beverages include carbonation through the use of carbon dioxide, caloric and noncaloric sweeteners, fruit and other acids such as phosphoric, malic and citric, and artificial and natural flavorings.

In another embodiment devices of the invention are used to generate materials for treating waste water, industrial effluent, cooling and boiler water, for chemical and biological contaminants and in combination with commonly used adjuncts. A wide range of biocidal agents including halogen based and nonhalogen based oxidizers are used. Preferred adjuncts include agents that minimize corrosion to equipment and retard mineral formation in and on system components.

In another embodiment, devices of the invention are used to prepare dietary, nutritional, and health and wellness materials, for ingestion by humans and animals. Preferred agents that can be prepared immediately prior to ingestion include organic colloids, inorganic, colloids, and combinations thereof. Preferred adjuncts include minerals, vitamins, aminoacids and chelates using these agents, probiotics and the like. Additionally, drugs and pharmaceuticals may be prepared in a similar manner or used as adjuncts in these systems. Exemplary adjuncts include pH modifiers, natural and artificial flavorings, sweeteners, and thickening agents. Chlorine dioxide is a preferred agent as it can be used to both disinfect natural biologics and botanicals which are contained by the devices and to treat the water for ingestion. Temperature in these systems can be manipulated by use of redox and neutralization reactions. Generation of nutritional substances in this manner avoids the chemical agents required to prepare tablets, gel coated materials, and agents required to increase the solubility of many natural substances. Materials generated with these devices have intimate contact with water as they never undergo a drying process and thus can provide greater bioavailability.

Many of the specific use embodiments described herein utilize devices that can be scaled and sized to meet the exact requirements of specific applications. Those experienced in the specific art associated with each of these specific use embodiments will understand the size of devices and concentrations of agents required to successfully address specific applications. Likewise, those experienced in the art will understand the adjuncts beneficial for each application and the inherent compatibilities of the materials, devices, and combinations thereof.

The invention disclosed is unique in that simple devices described are suitable for the preparation, manipulation, delivery, and storage of many different reactive agents that can be produced immediately prior to use. Significant economic and practical utility is provided by formulations that can address multiple different treatment operations. Preferred formulations involve the use of chlorine dioxide, minerals, and precipitates. Preferred formulations also provide the ability to simultaneously control fluids and supply reactive agents such as chlorine dioxide.

EXAMPLES

Example 1

A solution of sodium chlorite, technical grade, was placed in one of the precursor compartments in a device similar to that diagrammed in FIG. 3B. In the other compartment a solution of hydrochloric acid or citric acid was placed. The device and the precursor storage compartments were thermally sealed. Each of the precursor compartments contained a pressure sensitive barrier. Upon applying external pressure to both precursor compartments the liquids exited the storage compartments and mixed. Chlorine dioxide was formed immediately and the device contents were observed to have a yellow color, indicating readiness for use. The device was place into a refrigerator where it kept the enclosed space odor free for a period of four weeks. Over the four week period the yellow color of the device was slowly lost yielding only a transparent liquid, and indicating that the device was expended.

Similar devices were prepared and activated while completely submerged in water. Activation under water had no dilution effect on the device as there was no transport of water into or out of the device. When the device was held in a liquid fluid stream the fluid flowed around the device and not through it. Liquid streams containing suspended solids yielded similar results and no removal of suspended solids was observed, indicating the absence of a filter effect. Similar device tests were completed in an air stream with similar results.

Devices prepared with high concentrations of chlorine dioxide gas precursors yielded chlorine gas concentrations high enough to pressurize and expand the device. The generated gas diffused through the thin film package over time. Rapid release of the gas from the package was accomplished by tearing the package at a predefined site and generating an orifice.

Example 2

Generation of Mixed Phosphates and Carbonates

A solution of iron chloride was placed in one of the precursor compartment in a device similar to that diagrammed in FIG. 3. In the other compartment a solution of sodium phosphate was place. The device and the precursor storage compartments were heat sealed. Each of the precursor compartments contained a pressure sensitive barrier. Upon applying external pressure to both precursor compartments the liquids exited the storage chamber and mixed. Iron phosphate precipitates were formed immediately and the device contents were observed to have both turbidity and a light green color. Similar devices were prepared with soluble calcium, magnesium, phosphate and carbonate salts. These devices yielded mixed precipitates of the salts which were suitable as a calcium and magnesium dietary supplement. Similar devices were prepared containing calcium and magnesium carbonates, citric acid, malic acid and artificial sweetener. When reacted inside the device solutions of carbonates, citrates, malates, citrate malates, and carbon dioxide were generated, and suitable for dietary supplementation.

The invention claimed is:

1. A device for the generation, storage and delivery of a reactive gas comprising:
   one or more liquid impermeable polymer films, with a porosity sufficient to allow diffusion of a gas, sealed with a liquid impermeable seal to define an open volume space, and further sealed within the open volume space to define two or more reactive gas precursor storage compartments and a mixing compartment,
   wherein each reactive gas precursor storage compartment shares a common wall with an exterior wall of the device and a common wall with the mixing compartment,
   wherein at least a portion of the common wall with the mixing compartment comprises a pressure sensitive barrier, and
   wherein each reactive gas precursor storage compartment contains a reactive gas precursor.

2. The device of claim 1, wherein one or all of the two or more reactive gas precursor storage compartments further comprise one or more adjuncts.

3. The device of claim 2, wherein said adjuncts are selected from at least one of oxidizing agents, reducing agents, acids, bases, surfactants, foam controlling agents, fragrances, electrolytes, viscosity modifiers, thickeners, coloring agents, metal salts, emulsifiers, metal binding agents, heat generating agents, polymers, minerals, resins, metals, health and wellness agents, nutritional substances, botanicals, nutraceuticals, pharmaceuticals, vitamins, probiotics, mineral supplements, metals, chelated metals, plant extracts, animal extracts, and combinations thereof.

4. The device of claim 2, wherein the mixing compartment further comprises one or more adjuncts.

5. The device of claim 4, wherein the one or more adjuncts are selected from at least one of oxidizing agents, reducing agents, acids, bases, surfactants, foam controlling agents, fragrances, electrolytes, viscosity modifiers, thickeners, coloring agents, metal salts, emulsifiers, metal binding agents, heat generating agents, polymers, minerals, resins, metals, health and wellness agents, nutritional substances, botanicals, nutraceuticals, pharmaceuticals, vitamins, probiotics, mineral supplements, metals, chelated metals, plant extracts, animal extracts, and combinations thereof.

6. The device of claim 1, wherein the device further comprises a gas permeable thin film, a membrane, a controlled porosity packaging seal, a defined package orifice, or combinations thereof.

7. The device of claim 1 further comprising one or more integrated mixing elements selected from at least one of a hole, a slot, a permanent barrier, and combinations thereof.

8. The device of claim 1 wherein said polymer film is selected from at least one of flexible films, transparent films, laminated films, metal coated films, oxide coated films, opaque films, printed films, rigid films, oxygen barrier films, vapor barrier films, and food safe films.

9. The device of claim 1 further comprising one or more molded component selected from a nozzle, a plunger, a fluid connector, a fastener, a mounting clasp, and a surface cleaning enabling structure.

10. The device of claim 1, wherein said reactive gas precursors comprise at least one of a cation, an acid, an oxidation agent, a reduction agent, a base, an anion, a chelating agent, a precipitating agent, a flocculating agent, a metal salt, a dietary supplement, a nutritional supplement, and combinations thereof.

11. The device of claim 1 further comprising at least one fluid control material, wherein the fluid control material is selected from the group consisting of a particle, a fiber, a woven material, a non-woven material, a foam, a sponge or combinations thereof, capable of controlling solids, liquids, and gases contained in the device through fluid absorption.

12. The device of claim 11, wherein the particle or fiber is selected from a natural or synthetic organic polymer, a natural or synthetic inorganic polymer, a natural or synthetic mineral, or combinations thereof.

13. The device of claim 1 which contains a removable substrate for cleaning porous or nonporous surfaces, selected from the group containing, woven materials, nonwoven materials, sponges, foams, rubbers or combinations thereof.

14. The material of claim 13 which is used for absorbing a fluid or powder and treating absorbed fluid or powder.

15. A method for contaminant reduction using the device of claim 1 comprising; initiating generation of a reactive gas by applying an external pressure sufficient to breach the pressure sensitive barrier thereby allowing the reactive gas precursors stored in the reactive gas precursor storage compartments to mix, and placing the device on or near a target material.

16. The method of claim 15, wherein the target material is a porous or nonporous surface, a liquid solution, or a local volume of gas.

17. The method of claim 15, wherein the reactive gas is selected from at least one of chlorine, chlorine dioxide, chlorine monoxide, sulfur dioxide, carbon dioxide, bromine, iodine, oxygen, nitrogen, nitrogen monoxide, nitrogen dioxide, hydrogen sulfide, hydrogen cyanide, hydrogen and combinations thereof.

* * * * *